United States Patent
Bhatnagar et al.

(10) Patent No.: US 8,961,530 B2
(45) Date of Patent: Feb. 24, 2015

(54) IMPLANTATION SYSTEM FOR TISSUE REPAIR

(71) Applicant: JMEA Corporation, Rockville, MD (US)

(72) Inventors: Mohit K. Bhatnagar, Potomac, MD (US); Jack Y. Yeh, North Potomac, MD (US); James A. Sack, Elverson, PA (US)

(73) Assignee: JMEA Corporation, Rockville, MD (US)

( * ) Notice: Subject to any disclaimer, the term of this patent is extended or adjusted under 35 U.S.C. 154(b) by 0 days.

(21) Appl. No.: 14/075,009

(22) Filed: Nov. 8, 2013

(65) Prior Publication Data
US 2014/0135771 A1 May 15, 2014

Related U.S. Application Data

(60) Division of application No. 11/934,737, filed on Nov. 2, 2007, now Pat. No. 8,702,718, which is a continuation-in-part of application No. 11/117,704, filed on Apr. 29, 2005, now Pat. No. 7,632,313.

(51) Int. Cl.
*A61B 17/58* (2006.01)
*A61B 17/60* (2006.01)
*A61F 2/00* (2006.01)
(Continued)

(52) U.S. Cl.
CPC ........... *A61B 17/0642* (2013.01); *A61B 17/064* (2013.01); *A61B 17/068* (2013.01); *A61B 17/0682* (2013.01); *A61B 17/92* (2013.01); *A61F 2/0805* (2013.01); *A61F 2/0811* (2013.01); *A61B 17/0401* (2013.01); *A61B 17/0482* (2013.01); *A61B 2017/0409* (2013.01); *A61B 2017/0437* (2013.01); *A61B 2017/0472* (2013.01); *A61B 2017/0646* (2013.01); *A61F 2002/0858* (2013.01); *A61F 2002/0888* (2013.01)
USPC .......................................................... 606/99

(58) Field of Classification Search
USPC .......................................................... 606/99
See application file for complete search history.

(56) References Cited

U.S. PATENT DOCUMENTS

| | | |
|---|---|---|
| 2,881,762 A | 4/1959 | Lowrie |
| 3,875,595 A | 4/1975 | Froning |

(Continued)

FOREIGN PATENT DOCUMENTS

| | | |
|---|---|---|
| FR | 2651113 | 3/1991 |
| WO | 02058599 | 8/2002 |
| WO | 2006118930 | 11/2006 |

OTHER PUBLICATIONS

Notification Concerning Transmittal of International Preliminary Report on Patentability, mailed Apr. 9, 2009 in PCT Application No. PCT/US2006/015960.

(Continued)

*Primary Examiner* — Sameh Boles
(74) *Attorney, Agent, or Firm* — Plumsea Law Group, LLC

(57) ABSTRACT

A prosthesis delivery and implantation system for tissue repair is disclosed. The implantation system includes provisions for manually applying a prosthesis to a treatment area. This system may be applied to heal any imperfections in various different types of tissue. The system also provides provisions for independently inserting two end portions of the prosthesis into tissue.

24 Claims, 13 Drawing Sheets

(51) Int. Cl.
*A61B 17/064* (2006.01)
*A61B 17/068* (2006.01)
*A61B 17/92* (2006.01)
*A61F 2/08* (2006.01)
*A61B 17/04* (2006.01)

(56) References Cited

U.S. PATENT DOCUMENTS

| | | | |
|---|---|---|---|
| 4,006,747 A | 2/1977 | Kronenthal et al. | |
| 4,038,987 A | 8/1977 | Komiya | |
| 4,235,238 A | 11/1980 | Ogiu et al. | |
| 4,394,864 A | 7/1983 | Sandhaus | |
| 4,448,194 A | 5/1984 | DiGiovanni et al. | |
| 4,471,181 A | 9/1984 | Dennison | |
| 4,533,076 A | 8/1985 | Bourque | |
| 4,573,448 A | 3/1986 | Kambin | |
| 4,621,639 A | 11/1986 | Transue et al. | |
| 4,669,473 A | 6/1987 | Richards et al. | |
| 4,705,040 A | 11/1987 | Mueller et al. | |
| 4,724,840 A | 2/1988 | McVay et al. | |
| 4,873,976 A | 10/1989 | Schreiber | |
| 4,877,172 A | 10/1989 | Franklin et al. | |
| 4,884,572 A | 12/1989 | Bays et al. | |
| 4,950,285 A | 8/1990 | Wilk | |
| 4,997,436 A | 3/1991 | Oberlander | |
| 5,002,562 A | 3/1991 | Oberlander | |
| 5,085,661 A | 2/1992 | Moss | |
| 5,154,189 A | 10/1992 | Oberlander | |
| 5,192,326 A | 3/1993 | Bao et al. | |
| 5,222,961 A | 6/1993 | Nakao et al. | |
| 5,236,440 A | 8/1993 | Hlavacek | |
| 5,281,230 A | 1/1994 | Heidmueller | |
| 5,290,296 A | 3/1994 | Phillips | |
| 5,290,297 A | 3/1994 | Phillips | |
| 5,395,317 A | 3/1995 | Kambin | |
| 5,403,346 A | 4/1995 | Loeser | |
| 5,423,857 A | 6/1995 | Rosenman et al. | |
| 5,425,489 A | 6/1995 | Shichman et al. | |
| 5,439,464 A | 8/1995 | Shapiro | |
| 5,439,479 A | 8/1995 | Shichman et al. | |
| 5,445,167 A | 8/1995 | Yoon et al. | |
| 5,465,895 A | 11/1995 | Knodel et al. | |
| 5,470,337 A | 11/1995 | Moss | |
| 5,500,000 A | 3/1996 | Feagin et al. | |
| 5,527,321 A | 6/1996 | Hinchliffe | |
| 5,540,704 A | 7/1996 | Gordon et al. | |
| 5,549,679 A | 8/1996 | Kuslich | |
| 5,591,206 A | 1/1997 | Moufarrege | |
| 5,601,571 A | 2/1997 | Moss | |
| 5,632,433 A | 5/1997 | Grant et al. | |
| 5,643,319 A | 7/1997 | Green et al. | |
| 5,653,928 A | 8/1997 | Schnipke | |
| 5,716,416 A | 2/1998 | Lin | |
| 5,817,113 A | 10/1998 | Gifford, III et al. | |
| 5,827,298 A | 10/1998 | Hart et al. | |
| 5,836,147 A | 11/1998 | Schnipke | |
| 5,843,084 A | 12/1998 | Hart et al. | |
| 5,860,990 A | 1/1999 | Nobles et al. | |
| 5,931,855 A | 8/1999 | Buncke | |
| 5,941,439 A | 8/1999 | Kammerer et al. | |
| 5,954,747 A | 9/1999 | Clark | |
| 5,972,005 A | 10/1999 | Stalker et al. | |
| 5,976,186 A | 11/1999 | Bao et al. | |
| 5,980,504 A | 11/1999 | Sharkey et al. | |
| 5,993,475 A | 11/1999 | Lin et al. | |
| 5,997,552 A | 12/1999 | Person et al. | |
| 6,010,513 A | 1/2000 | Tormala et al. | |
| 6,039,753 A | 3/2000 | Meislin | |
| 6,074,395 A | 6/2000 | Trott et al. | |
| 6,099,514 A | 8/2000 | Sharkey et al. | |
| 6,110,210 A | 8/2000 | Norton et al. | |
| 6,126,670 A | 10/2000 | Walker et al. | |
| 6,126,682 A | 10/2000 | Sharket et al. | |
| 6,146,387 A | 11/2000 | Trott et al. | |
| 6,156,039 A | 12/2000 | Thal | |
| 6,183,518 B1 | 2/2001 | Ross et al. | |
| 6,190,401 B1 | 2/2001 | Green et al. | |
| 6,206,921 B1 | 3/2001 | Guagliano et al. | |
| 6,206,923 B1 | 3/2001 | Boyd et al. | |
| 6,241,747 B1 | 6/2001 | Ruff | |
| 6,245,107 B1 | 6/2001 | Ferree | |
| 6,264,659 B1 | 7/2001 | Ross et al. | |
| 6,270,517 B1 | 8/2001 | Brotz | |
| 6,280,475 B1 | 8/2001 | Bao et al. | |
| 6,290,715 B1 | 9/2001 | Sharkey et al. | |
| 6,306,156 B1 | 10/2001 | Clark | |
| 6,318,553 B1 | 11/2001 | Deschenes | |
| 6,322,563 B1 | 11/2001 | Cummings et al. | |
| 6,332,894 B1 | 12/2001 | Stalcup et al. | |
| 6,387,113 B1 | 5/2002 | Hawkins et al. | |
| 6,387,130 B1 | 5/2002 | Stone et al. | |
| 6,395,031 B1 | 5/2002 | Foley et al. | |
| 6,402,750 B1 | 6/2002 | Atkinson et al. | |
| 6,425,919 B1 | 7/2002 | Lambrecht | |
| 6,427,895 B1 | 8/2002 | Deschenes | |
| 6,428,576 B1 | 8/2002 | Haldimann | |
| 6,443,988 B2 | 9/2002 | Felt et al. | |
| 6,446,854 B1 | 9/2002 | Remiszewski | |
| 6,482,235 B1 | 11/2002 | Lambrecht et al. | |
| 6,491,724 B1 | 12/2002 | Ferree | |
| 6,494,886 B1 | 12/2002 | Wilk et al. | |
| 6,497,707 B1 | 12/2002 | Bowman et al. | |
| 6,508,839 B1 | 1/2003 | Lambrecht et al. | |
| 6,517,568 B1 | 2/2003 | Sharkey et al. | |
| 6,530,933 B1 | 3/2003 | Yeung et al. | |
| 6,551,343 B1 | 4/2003 | Tormala et al. | |
| 6,562,033 B2 | 5/2003 | Shah et al. | |
| 6,564,939 B1 | 5/2003 | Deschenes et al. | |
| 6,569,369 B2 | 5/2003 | Shilale et al. | |
| 6,579,291 B1 | 6/2003 | Keith et al. | |
| 6,592,625 B2 | 7/2003 | Cauthen | |
| 6,596,008 B1 | 7/2003 | Kambin | |
| 6,596,014 B2 | 7/2003 | Levinson et al. | |
| 6,599,310 B2 | 7/2003 | Leung et al. | |
| 6,602,291 B1 | 8/2003 | Rya et al. | |
| 6,638,276 B2 | 10/2003 | Sharkey et al. | |
| 6,666,872 B2 | 12/2003 | Barreiro et al. | |
| 6,676,678 B2 | 1/2004 | Gifford, III et al. | |
| 6,682,535 B2 | 1/2004 | Hoogland | |
| 6,685,077 B1 | 2/2004 | Davignon et al. | |
| 6,689,125 B1 | 2/2004 | Keith et al. | |
| 6,692,499 B2 | 2/2004 | Tormala et al. | |
| 6,709,442 B2 | 3/2004 | Miller et al. | |
| 6,719,763 B2 | 4/2004 | Chung et al. | |
| 6,726,685 B2 | 4/2004 | To et al. | |
| 6,733,496 B2 | 5/2004 | Sharkey et al. | |
| 6,733,531 B1 | 5/2004 | Trieu | |
| 6,736,815 B2 | 5/2004 | Ginn | |
| 6,746,685 B2 | 6/2004 | Williams | |
| 6,755,843 B2 | 6/2004 | Chung et al. | |
| 6,776,784 B2 | 8/2004 | Ginn | |
| 6,779,701 B2 | 8/2004 | Bailly et al. | |
| 6,805,695 B2 | 10/2004 | Keith et al. | |
| 6,848,152 B2 | 2/2005 | Genova et al. | |
| 7,004,970 B2 | 2/2006 | Cauthen, III et al. | |
| 7,052,516 B2 | 5/2006 | Cauthen, III et al. | |
| 7,056,330 B2 | 6/2006 | Gayton | |
| 7,189,235 B2 | 3/2007 | Cauthen | |
| 7,338,502 B2 | 3/2008 | Rosenblatt | |
| 7,547,326 B2 | 6/2009 | Bhatnagar et al. | |
| 7,608,108 B2 | 10/2009 | Bhatnagar et al. | |
| 7,632,313 B2 | 12/2009 | Bhatnagar et al. | |
| 8,070,818 B2 | 12/2011 | Bhatnagar et al. | |
| 8,177,847 B2 | 5/2012 | Bhatnagar et al. | |
| 8,702,718 B2 | 4/2014 | Batnagar et al. | |
| 2001/0004710 A1 | 6/2001 | Felt et al. | |
| 2001/0010021 A1 | 7/2001 | Boyd et al. | |
| 2002/0019626 A1 | 2/2002 | Sharkey et al. | |
| 2002/0019636 A1 | 2/2002 | Ogilvie et al. | |
| 2002/0022830 A1 | 2/2002 | Sharkey et al. | |
| 2002/0026195 A1 | 2/2002 | Layne et al. | |
| 2002/0068974 A1 | 6/2002 | Kuslich et al. | |
| 2002/0111688 A1 | 8/2002 | Cauthen | |
| 2002/0120337 A1 | 8/2002 | Cauthen | |

(56) References Cited

U.S. PATENT DOCUMENTS

| | | |
|---|---|---|
| 2002/0123807 A1 | 9/2002 | Cauthen, III |
| 2002/0147461 A1 | 10/2002 | Aldrich et al. |
| 2002/0147479 A1 | 10/2002 | Aldrich |
| 2002/0147496 A1 | 10/2002 | Belef et al. |
| 2002/0147497 A1 | 10/2002 | Belef et al. |
| 2002/0151976 A1 | 10/2002 | Foley et al. |
| 2002/0151979 A1 | 10/2002 | Lambrecht et al. |
| 2002/0151980 A1 | 10/2002 | Cauthen |
| 2002/0156530 A1 | 10/2002 | Lambrecht et al. |
| 2002/0156531 A1 | 10/2002 | Felt et al. |
| 2002/0165542 A1 | 11/2002 | Ferree |
| 2002/0173851 A1 | 11/2002 | McKay |
| 2002/0183848 A1 | 12/2002 | Ray et al. |
| 2002/0189622 A1 | 12/2002 | Cauthen, III et al. |
| 2002/0198599 A1 | 12/2002 | Haldimann |
| 2003/0009227 A1 | 1/2003 | Lambrecht et al. |
| 2003/0014117 A1 | 1/2003 | Lambrecht et al. |
| 2003/0014118 A1 | 1/2003 | Lambrecht et al. |
| 2003/0014177 A1 | 1/2003 | Lambrecht et al. |
| 2003/0028251 A1 | 2/2003 | Mathews |
| 2003/0040796 A1 | 2/2003 | Ferree |
| 2003/0069641 A1 | 4/2003 | Reuter et al. |
| 2003/0074075 A1 | 4/2003 | Thomas, Jr. et al. |
| 2003/0078579 A1 | 4/2003 | Ferree |
| 2003/0082169 A1 | 5/2003 | Boyd |
| 2003/0083642 A1 | 5/2003 | Boyd et al. |
| 2003/0093155 A1 | 5/2003 | Lambrecht et al. |
| 2003/0114930 A1 | 6/2003 | Lim et al. |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0153976 A1 | 8/2003 | Cauthen, III et al. |
| 2003/0158604 A1 | 8/2003 | Cauthen, III et al. |
| 2003/0163200 A1 | 8/2003 | Cauthen |
| 2003/0167055 A1 | 9/2003 | Kolata et al. |
| 2003/0181964 A1 | 9/2003 | Sharkey et al. |
| 2003/0181983 A1 | 9/2003 | Cauthen |
| 2003/0187445 A1 | 10/2003 | Keith et al. |
| 2003/0187507 A1 | 10/2003 | Cauthen |
| 2003/0187508 A1 | 10/2003 | Cauthen |
| 2003/0191436 A1 | 10/2003 | Ferree |
| 2003/0191536 A1 | 10/2003 | Ferree |
| 2003/0195514 A1 | 10/2003 | Trieu et al. |
| 2003/0195628 A1 | 10/2003 | Bao et al. |
| 2003/0195630 A1 | 10/2003 | Ferree |
| 2003/0199979 A1 | 10/2003 | McGuckin, Jr. |
| 2003/0199984 A1 | 10/2003 | Trieu |
| 2003/0220649 A1 | 11/2003 | Bao et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2003/0220695 A1 | 11/2003 | Sevrain |
| 2004/0002746 A1 | 1/2004 | Ryan et al. |
| 2004/0002760 A1 | 1/2004 | Boyd et al. |
| 2004/0002763 A1 | 1/2004 | Phillips et al. |
| 2004/0002764 A1 | 1/2004 | Gainor et al. |
| 2004/0010317 A1 | 1/2004 | Lambrecht et al. |
| 2004/0019381 A1 | 1/2004 | Pflueger |
| 2004/0024463 A1 | 2/2004 | Thomas, Jr. et al. |
| 2004/0024465 A1 | 2/2004 | Lambrecht et al. |
| 2004/0030392 A1 | 2/2004 | Lambrecht et al. |
| 2004/0034429 A1 | 2/2004 | Lambrecht et al. |
| 2004/0039392 A1 | 2/2004 | Trieu |
| 2004/0044412 A1 | 3/2004 | Lamrecht et al. |
| 2004/0059417 A1 | 3/2004 | Smith et al. |
| 2004/0059418 A1 | 3/2004 | McKay et al. |
| 2004/0064023 A1 | 4/2004 | Ryan et al. |
| 2004/0068268 A1 | 4/2004 | Boyd et al. |
| 2004/0073308 A1 | 4/2004 | Kuslich et al. |
| 2004/0083002 A1 | 4/2004 | Belef et al. |
| 2004/0092933 A1 | 5/2004 | Shaolian et al. |
| 2004/0092945 A1 | 5/2004 | Ferree |
| 2004/0097924 A1 | 5/2004 | Lambrecht et al. |
| 2004/0097980 A1 | 5/2004 | Ferree |
| 2004/0102774 A1 | 5/2004 | Trieu |
| 2004/0138705 A1* | 7/2004 | Heino et al. ............ 606/219 |
| 2004/0267309 A1 | 12/2004 | Garvin |
| 2005/0055027 A1 | 3/2005 | Yeung et al. |
| 2005/0070924 A1 | 3/2005 | Schaller et al. |
| 2005/0288689 A1* | 12/2005 | Kammerer et al. ......... 606/142 |
| 2006/0247643 A1 | 11/2006 | Bhatnagar et al. |
| 2006/0247644 A1 | 11/2006 | Bhatnagar et al. |
| 2007/0088438 A1 | 4/2007 | Cauthen, III et al. |
| 2007/0100348 A1 | 5/2007 | Cauthen, III et al. |
| 2007/0100354 A1 | 5/2007 | Cauthen, III et al. |
| 2007/0149987 A1 | 6/2007 | Wellman et al. |
| 2007/0185497 A1 | 8/2007 | Cauthen |
| 2009/0118734 A1 | 5/2009 | Bhatnagar et al. |
| 2010/0057145 A1 | 3/2010 | Bhatnagar et al. |
| 2011/0071548 A1 | 3/2011 | Yeh et al. |
| 2011/0295258 A9 | 12/2011 | Bhatnagar et al. |

OTHER PUBLICATIONS

International Search Report and The Written Opinion of the International Searching Authority, mailed Jan. 17, 2011 in PCT Application No. PCT/US2010/049613.
Notification Concerning Transmittal of International Preliminary Report on Patentability, mailed Apr. 5, 2012 in PCT Application No. PCT/US2010/049613.
Office Action from U.S. Appl. No. 12/413,113, mailed Jun. 30, 2011.
Response to Office Action filed on Sep. 22, 2011 for U.S. Appl. No. 12/413,113.
Notice of Allowance from U.S. Appl. No. 12/413,113 mailed Oct. 7, 2011.
Office Action from U.S. Appl. No. 12/564,323, mailed Aug. 9, 2011.
Response to Office Action filed on Nov. 17, 2011 for U.S. Appl. No. 12/564,323.
Final Office Action from U.S. Appl. No. 12/564,323, mailed Dec. 21, 2011.
Response to Final Office Action filed on Feb. 21, 2012 for U.S. Appl. No. 12/564,323.
Notice of Allowance from U.S. Appl. No. 12/564,323 mailed Mar. 7, 2012.
Final Office Action from U.S. Appl. No. 11/117,704, mailed Nov. 26, 2008.
Amendment Accompanying Request for Continued Examination filed on May 22, 2009 for U.S. Appl. No. 11/117,704.
Request for Continued Examination filed May 22, 2009 for U.S. Appl. No. 11/117,704.
Notice of Allowance from U.S. Appl. No. 11/117,704 mailed Aug. 7, 2009.
Amendment Accompanying Request for Continued Examination filed on Jun. 24, 2008 for U.S. Appl. No. 11/379,940.
Request for Continued Examination filed Jun. 24, 2008 for U.S. Appl. No. 11/379,940.
Office Action from U.S. Appl. No. 11/379,940 mailed Sep. 19, 2008.
Response to Office Action filed on Dec. 19, 2008 for U.S. Appl. No. 11/379,940.
Notice of Allowance from U.S. Appl. No. 11/379,940 mailed Jun. 12, 2009.
Supplemental Notice of Allowability from U.S. Appl. No. 11/379,940 mailed Aug. 18, 2009.
Office Action from U.S. Appl. No. 11/324,765 mailed Sep. 5, 2008.
Amendment and Response to Office Action filed on Dec. 5, 2008 for U.S. Appl. No. 11/324,765.
Amendment Pursuant to 37 C.F.R. 1.312 filed on Mar. 4, 2009 for U.S. Appl. No. 11/324,765.
Amendment Pursuant to 37 C.F.R. 1.312 filed on Mar. 20, 2009 for U.S. Appl. No. 11/324,765.
Response to Rule 312 Communication from U.S. Appl. No. 11/324,765 mailed Mar. 24, 2009.
Response to Rule 312 Communication from U.S. Appl. No. 11/324,765 mailed May 5, 2009.
International Search Report from related PCT application (International Application No. PCT/US2006/015960), dated Apr. 23, 2008.
Office Action from U.S. Appl. No. 11/117,704 mailed Sep. 21, 2007.
Response to Office Action filed on Jan. 22, 2008 for U.S. Appl. No. 11/117,704.

(56) References Cited

OTHER PUBLICATIONS

Final Office Action from U.S. Appl. No. 11/117,704 mailed May 16, 2008.
Response to Final Office Action filed on Jun. 20, 2008 for U.S. Appl. No. 11/117,704.
Office Action from U.S. Appl. No. 11/117,704 mailed Jul. 24, 2008.
Response to Office Action filed on Aug. 8, 2008 for U.S. Appl. No. 11/117,704.
Notice of Allowance from U.S. Appl. No. 11/324,765 mailed Mar. 9, 2009.
Notice of Allowability from U.S. Appl. No. 11/324,765 mailed Feb. 24, 2009.
Office Action from U.S. Appl. No. 11/379,940 mailed Sep. 21, 2007.
Response to Office Action filed on Jan. 22, 2008 for U.S. Appl. No. 11/379,940.
Final Office Action from the U.S. Appl. No. 11/379,940. mailed Apr. 30, 2008.
Amendment Accompanying Request for Continued Examination mailed May 21, 2012 for U.S. Appl. No. 11/934,737, filed Nov. 2, 2007.
Amendment mailed Mar. 3, 2009 for U.S. Appl. No. 11/324,765, filed Jan. 3, 2006.
Decision Granting Petition mailed Aug. 24, 2011 for U.S. Appl. No. 11/934,737 filed Nov. 2, 2007.
Final Office Action mailed Dec. 20, 2011 for U.S. Appl. No. 11/934,737, filed Nov. 2, 2007.
Notice of Allowance mailed Dec. 16, 2011 for U.S. Appl. No. 12/612,970, filed Nov. 5, 2009.
Notice of Allowance mailed Sep. 28, 2011 for U.S. Appl. No. 12/612,970, filed Nov. 5, 2009.
Office Action mailed May 11, 2011 for U.S. Appl. No. 11/934,737 filed Nov. 2, 2007.
Request for Continued Examination mailed Nov. 2, 2011 for U.S. Appl. No. 12/612,970, filed Nov. 5, 2009.
Request for Continued Examination mailed May 21, 2012 for U.S. Appl. No. 11/934,737, filed Nov. 2, 2007.
Response to Office Action mailed on Jul. 25, 2011 for U.S. Appl. No. 11/934,737, filed Nov. 2, 2007.
Robinson, Raymond P., MD, "The Early Innovators of Today's Resurfacing Condylar Knees," The Journal of Arthroplasty, vol. 20, No. 1., Suppl. 1 2005.

\* cited by examiner

IMPLANTATION SYSTEM FOR TISSUE REPAIR

CROSS REFERENCE TO RELATED APPLICATIONS

This application is a division of U.S. Patent Publication Number US 2011/0295258 A9 (U.S. application Ser. No. 11/934,737, filed Nov. 2, 2007), which is a continuation-in-part of U.S. Pat. No. 7,632,313, issued Dec. 15, 2009 (U.S. application Ser. No. 11/117,704, filed Apr. 29, 2005), both of which are herein incorporated by reference in their entirety.

BACKGROUND

1. Field

The present invention relates generally to implantation systems and in particular to a manual implantation system for tissue repair.

2. Description of Related Art

Currently, closure prostheses for repairing tears, cuts, holes or other imperfections in tissue operate by inserting two ends of a closure prosthesis into the tissue simultaneously, in effect "stapling" the prosthesis into place. Other known systems provide two different prostheses that include integrated stitches. Using this system, the doctor must implant both prostheses in different locations, grasp the loose ends of the stitches and then laboriously and manually tie or knot the stitches together. Current methods for implanting closure prostheses lack provisions to increase precision in the delivery of the prosthesis and to provide for increased control of implantation. There is a need in the art for a design that solves many of the problems of the prior art.

SUMMARY

A method and apparatus for implanting a prosthesis for repairing tissue are disclosed. In one aspect, the invention provides a prosthesis delivery and implantation system comprising: a delivery cannula having a distal end portion, the distal end portion of the delivery lumen configured for placement near a treated area; the delivery cannula having a delivery lumen configured to accommodate a prosthesis delivery system; the prosthesis delivery and implantation system including a first delivery needle and a second delivery needle; and a spacing web disposed between the first delivery needle and the second delivery needle; wherein the prosthesis delivery and implantation system is configured to retain and deliver the prosthesis; the prosthesis having a first end portion, a central portion and a second end portion; the first delivery needle being generally hollow and having a first open channel configured to accommodate the first end portion of the prosthesis; the second delivery needle also being generally hollow and having a second open channel configured to accommodate the second end portion of the prosthesis; a first impact member disposed within the first open channel of the first delivery needle; wherein the impact member transfers a first force to the first end portion of the prosthesis; a second impact member disposed within the second open portion of the second delivery needle; and wherein the second impact member transfers a second force to the second end portion of the prosthesis.

In another aspect, the first impact member and the second impact member are rigidly associated and the two impact members can be driven generally simultaneously.

In another aspect, the first impact member and the second impact member are capable of relative motion with respect to one another and wherein the first impact member may be moved independent of the second impact member.

In another aspect, distal motion of the first impact member displaces the first end portion of the prosthesis distally and eventually displaces the first end portion of the prosthesis from the first delivery needle and implants the first end portion of the prosthesis into a tissue.

In another aspect, the central portion of the prosthesis is flexible and accommodates relative motion between the first end portion of the prosthesis and the end portion of the prosthesis.

In another aspect, the second end portion of the prosthesis is displaced distally away from the second delivery needle by the second impact member after the first end portion of the prosthesis is implanted.

In another aspect, the first impact member includes a distal end portion configured to contact the first end portion of the prosthesis; and a proximal end portion configured to receive the first force.

In another aspect, the invention provides a method for implanting a prosthesis comprising the steps of: moving a delivery cannula into position near a tissue to be treated; loading the prosthesis into a prosthesis delivery and implantation system; moving the prosthesis delivery and implantation system into a delivery lumen of a delivery cannula; moving the prosthesis delivery and implantation system near the tissue to be treated; implanting a first end portion of the prosthesis into the tissue; and implanting a second end portion of the prosthesis into the tissue.

In another aspect, the step of moving the prosthesis delivery and implantation system into the delivery lumen of the delivery cannula is performed before the step of moving the delivery cannula into position near the tissue.

In another aspect, the step of loading the prosthesis into a prosthesis delivery and implantation system includes the steps of: placing a first end portion of the prosthesis into a first open channel of a first delivery needle; and placing a second end portion of the prosthesis into a second open channel of a second delivery needle.

In another aspect, further comprising the step of moving the prosthesis distally towards the tissue.

In another aspect, wherein the prosthesis is moved distally by moving a first impact member disposed within a first open channel of a first delivery needle and by moving a second impact member disposed within a second open channel of a second delivery needle.

In another aspect, the first impact member and the second impact member are rigidly associated and the two impact members can be driven generally simultaneously.

In another aspect, the first impact member and the second impact member can be driven independently.

In another aspect, the invention provides a prosthesis delivery and implantation system comprising: a delivery cannula having a distal end portion, the distal end portion of the delivery lumen configured for placement near a treated area; the delivery cannula having a delivery lumen configured to accommodate a prosthesis delivery system; the prosthesis delivery and implantation system including a first delivery needle and a second delivery needle; and a spacing web disposed between the first delivery needle and the second delivery needle; wherein the prosthesis delivery system is configured to retain and deliver the prosthesis; the prosthesis having a first end portion, a central portion and a second end portion; the first delivery needle being generally hollow and having a first open channel configured to accommodate the first end portion of the prosthesis; the second delivery needle also being generally hollow and having a second open channel configured to accommodate the second end portion of the prosthesis; and wherein the first end portion is implanted substantially prior to the implantation of the second end portion.

In another aspect, the prosthesis is moved distally by moving a first impact member disposed within a first open channel of a first delivery needle and by moving a second impact member disposed within a second open channel of a second delivery needle.

In another aspect, a first force is applied to the first impact member.

In another aspect, a second force is applied to the second impact member after the first force has been applied to the first impact member.

In another aspect, the prosthesis may be applied to a detached tendon and reconnect the tendon to an associated bone.

In another aspect, the prosthesis may be used to repair a meniscus.

In another aspect, the prosthesis may be used to repair a tear associated with an injury to a rotator cuff.

In another aspect, the prosthesis may be used to attach a first portion of bone to a second portion of bone.

In another aspect, the invention provides a prosthesis delivery and implantation system comprising: a prosthesis having a first end portion, a central portion and a second end portion; a first impact member having a first distal end configured to associate and align with the first end portion; wherein the impact member transfers a first force to the first end portion of the prosthesis; a second impact member having a second distal end configured to associate and align with the second end portion; and wherein the second impact member transfers a second force to the second end portion of the prosthesis.

In another aspect, the invention provides a method for implanting a prosthesis comprising the steps of: loading the prosthesis into a prosthesis delivery and implantation system; moving the prosthesis delivery and implantation system near the tissue to be treated; implanting a first end portion of the prosthesis into the tissue; and implanting a second end portion of the prosthesis into the tissue.

Other systems, methods, features and advantages of the invention will be, or will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
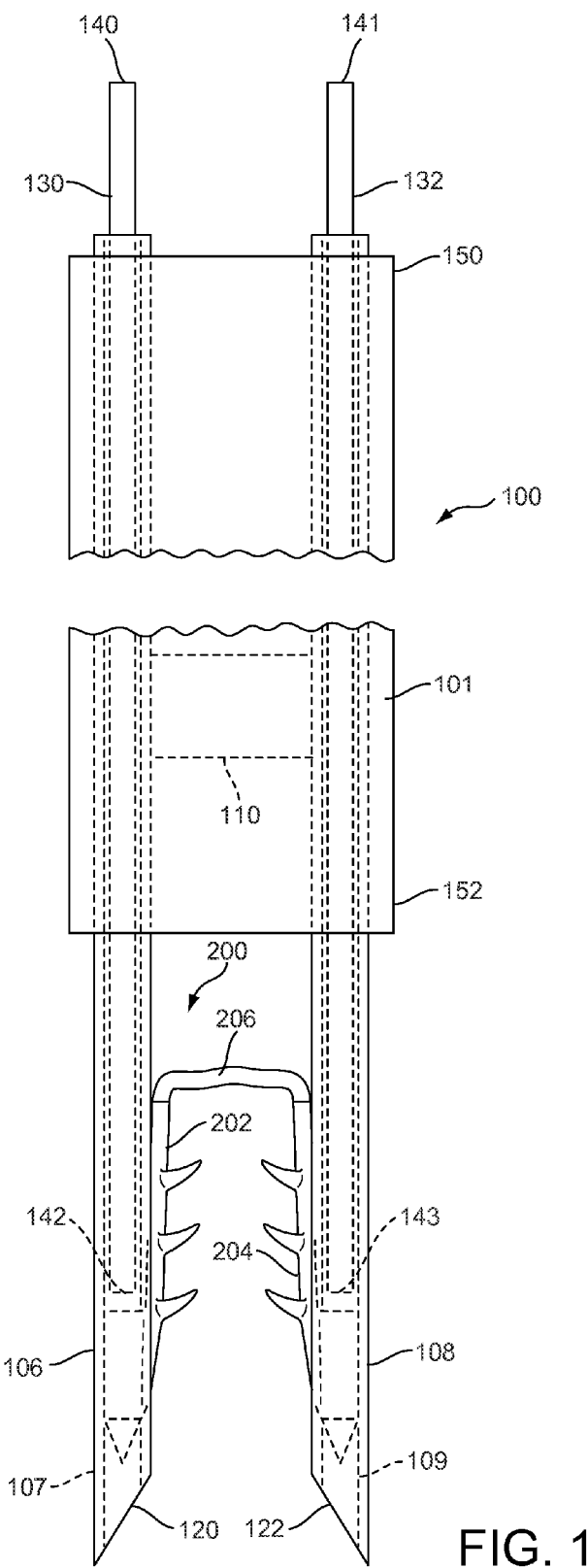
FIG. 1 is a plan view of a preferred embodiment of a prosthesis delivery and implantation system.
Figure 2:
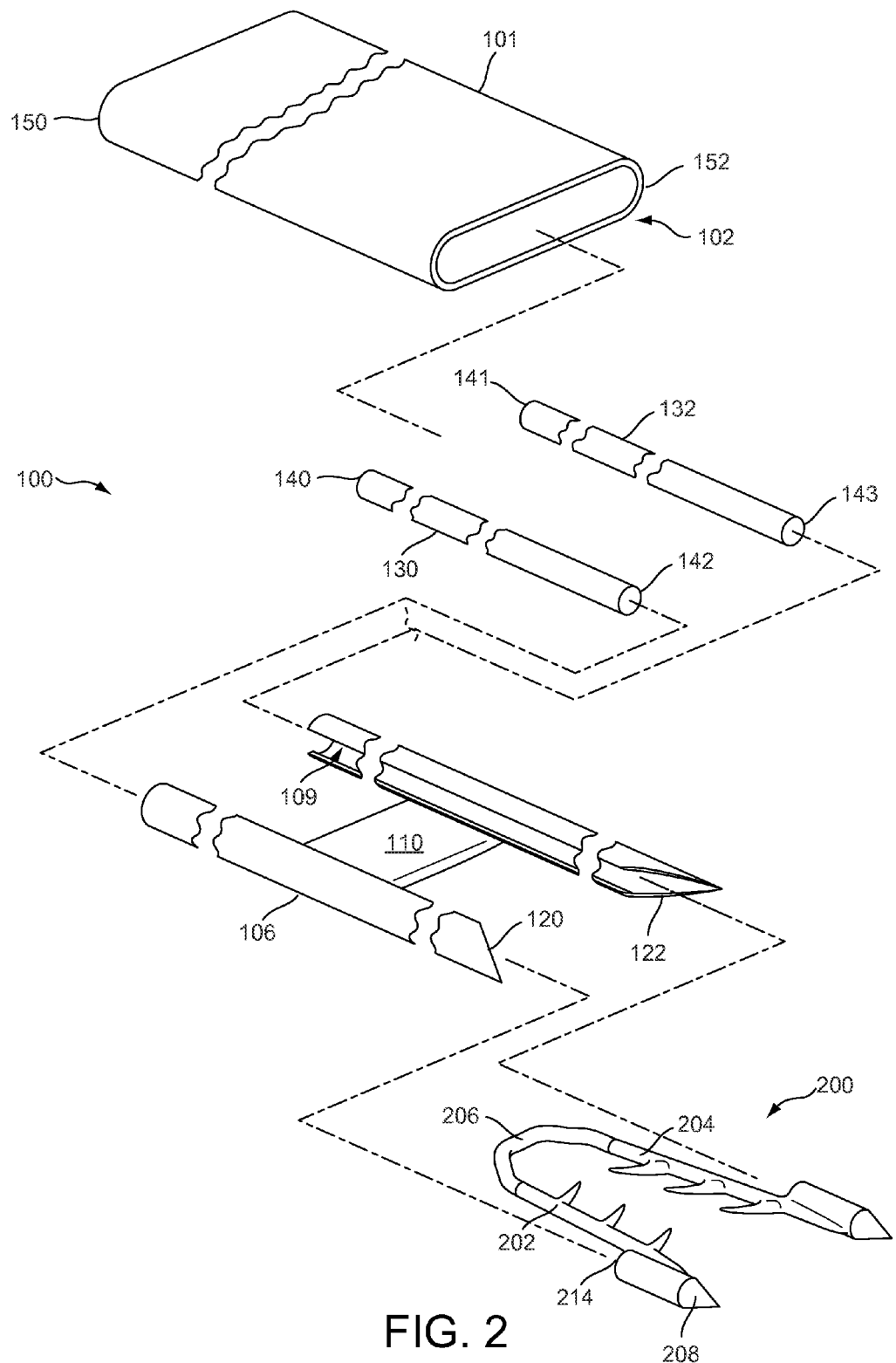
FIG. 2 is an isometric view of a preferred embodiment of a prosthesis delivery and implantation system.

FIGS. 1-2 illustrate one embodiment of prosthesis delivery and implantation system 100, hereby referred to as PDI system 100. Specifically, FIG. 1 is a plan view of a preferred embodiment of PDI system 100 and FIG. 2 is an exploded isometric view of a preferred embodiment of PDI system 100. Generally, PDI system 100 may be used for repairing any flaw, imperfection, cut, incision, hole, or tear in various types of tissue throughout the human body. The term "tissue" as used throughout this detailed description and in the claims refers to any collection of interconnected cells that perform a similar function within an organism. Examples of different types of biological tissue include epithelium, connective tissue (such as bone), muscle tissue and nervous tissue.

In this embodiment, PDI system 100 may be associated with delivery cannula 101. Generally, delivery cannula 101 may be any type of tube that is configured to insert into the body and may include one or more channels for delivering one or more devices. In this preferred embodiment, delivery cannula 101 includes delivery lumen 102 for accommodating PDI system 100. Delivery cannula 101 and delivery lumen 102 preferably both include distal end portion 152 that is configured to be placed near a treatment area of one or more tissues.

PDI system 100 preferably comprises several components configured to deliver and implant prosthesis 200 into some kind of tissue in need of repair. Although one particular embodiment of prosthesis 200 is illustrated in these figures, the size, shape, and other characteristics of the individual components comprising prosthesis 200 may be determined based on a number of factors, potentially including the size and shape of the imperfection; the condition and type of tissue that may be repaired using prosthesis 200; and the type and amount of circumferential or other stress that is to be exerted by prosthesis 200 on the surrounding tissue during the implantation process.

Prosthesis 200 may comprise first end portion 202 and second end portion 204 that are joined by central portion 206. End portions 202 and 204 each include relatively pointed ends 208. Along the length of the end portions 202 and 204 behind pointed ends 208 are a number of projections 212 that extend inwardly and rearwardly, such that their free ends generally point towards central portion 206. Although only a few projections 212 are shown in FIGS. 1 and 2, in other embodiments, prosthesis 200 may include any number of projections 212, arranged over all or part of prosthesis 200, including both first and second end portions 202, 204 and connecting portion 206. In still other embodiments, projections 212 can also be arranged in different planes.

In some embodiments, pointed ends 208 may also anchor prosthesis 200. For example, the relatively larger back portion 214 of pointed ends 208 may also help to anchor end portions 202 and 204 of prosthesis 200. In other embodiments, pointed ends 208 could have a different shape that is configured to facilitate implantation and anchoring of prosthesis 200.

Central portion 206 of prosthesis 200 extends between first end portion 202 and second end portion 204 and connects first end portion 202 with second end portion 204. In some embodiments, central portion 206 may provide a rigid connection between end portions 202 and 204. In other embodiments, however, central portion 206 may be flexible and configured to allow for relative motion of first end portion 202 with respect to second end portion 204. In some cases, central portion 206 may be pulled taut between end portions 202 and 204. In other cases, central portion 206 can be partially slack between end portions 202 and 204.

Further examples of prostheses of the type discussed here can be found in U.S. 2006/0247643, which is hereby incorporated by reference.

PDI system 100 also preferably includes first delivery needle 106 and second delivery needle 108. In this embodiment, delivery needles 106 and 108 may disposed within delivery lumen 102. In some embodiments, delivery needles 106 and 108 are generally hollow. In a preferred embodiment, delivery needles 106 and 108 may be partially opened. In particular, first delivery needle 106 may include first open channel 107. Also, second delivery needle 108 may include second open channel 109. In a preferred embodiment, channels 107 and 109 have C-shaped cross sections. The C-shaped cross section of second open channel 109 can be clearly seen in FIG. 2. Preferably, first open channel 107 has a similar C-shaped cross section. With this configuration, open channels 107 and 109 are configured to receive prosthesis 200 in a manner that allows prosthesis 200 to slide between delivery needles 106 and 108 while allowing first end portion 202 and second end portion 204 to be partially restrained within first delivery needle 106 and second delivery needle 108, respectively.

Delivery needles 106 and 108 may also include tapered ends configured to contact, and some cases penetrate through tissue. In this embodiment, first delivery needle 106 and second delivery needle 108 may include first needle end 120 and second needle end 122, respectively. In a preferred embodiment, needle ends 120 and 122 are tapered to provide sharpened tips. In some cases, this tapered configuration of needle ends 120 and 122 may provide for wider openings of open channels 107 and 109.

In some embodiments, delivery needles 106 and 108 may be connected via spacing web 110 disposed between delivery needles 106 and 108. In some cases, spacing web 110 may be attached to delivery needles 106 and 108 on outer surfaces of delivery needles 106 and 108 that are disposed away from open channels 107 and 109. This arrangement preferably helps prevent spacing web 110 from interfering with one or more components disposed within open channels 107 and 109.

In some cases, spacing web 110 may provide for a rigid connection between delivery needles 106 and 108. In other cases, spacing web 110 may provide for a loose connection between delivery needles 106 and 108. With this arrangement, spacing web 110 may be configured to prevent delivery needles 106 and 108 from separating beyond a predetermined distance that would allow prosthesis 200 to slide out of open channels 107 and 109.

Preferably, PDI system 100 includes provisions for applying a force to prosthesis 200 for implantation into various types of tissue. In some embodiments, PDI system 100 may be associated with first impact member 130 and second impact member 132. Impact members 130 and 132 are preferably configured to insert into open channels 107 and 109. In a preferred embodiment, impact members 130 and 132 are substantially rigid and configured to transfer a force applied at first proximal end portion 140 and second proximal end portion 141 to first distal end portion 142 and second distal end portion 143, respectively. With this arrangement, impact members 130 and 132 may be used to transfer an insertion force to first end portion 202 and second end portion 204 of prosthesis 200. In particular, first impact member 130 may transfer a first force to first end portion 202 and second impact member 132 may transfer a second force to second end portion 204.

In some embodiments, first impact member 130 and second impact member 132 may be rigidly connected using one or more connecting members. Provisions for connecting impact members 130 and 132 are discussed below. This may help apply forces to end portions 202 and 204 simultaneously. In other embodiments, impact members 130 and 132 may not be rigidly attached and may be capable of relative motion with respect to one another. In these embodiments, a force must be applied to each impact member 130 and 132 separately to implant end portions 202 and 204.

Generally, various different types of materials may be used for making PDI system 100. Preferably, delivery needles 106 and 108 may be made of rigid materials. Likewise, impact members 130 and 132 may also be made of rigid materials. In some cases, rigid plastics may be used. In other cases, materials may be used that include some type of metal.

In some embodiments, portions of prosthesis 200 may be made of a generally rigid material. Other portions of prosthesis 200 may be made of a generally flexible material. In a preferred embodiment, end portions 202 and 204 are made of a generally rigid material and central portion 206 is made of a generally flexible material. Using a rigid material may help facilitate insertion of prosthesis 200 into various types of tissue. In some cases, prosthesis 200 could be made of a material including metal. In other embodiments, however, prosthesis 200 could be made of other materials. In other cases, for example, it may be preferable to make prosthesis 200 using a biocompatible material that is sufficiently rigid to hold a cut or incision in some types of tissue closed, yet sufficiently compliant so as to avoid further damaging the tissue should slight relative motion between the tissue and prosthesis 200 occur. Examples of suitable materials include nylon, prolene, dacron, ultra high molecular weight polyethylene (UHMWPE), and other suitable suture materials. In a preferred embodiment, prosthesis 200 may be made of a material including at least one type of metal.

In still other embodiments, prosthesis 200 may be formed of a bioabsorbable polymer that is gradually absorbed by the body. Some examples of suitable bioabsorbable materials are: poly L-lactic acid (PLLA), polyglycolic acid (PGA). Closure prosthesis can also be formed of other possible materials, including polytetrafluorethylene (PTFE), polyaryletherketone (PAEK), polyetheretherketone (PEEK), polyoxymethylene (acetal), polycarbonate, polysulfone, silicone elastomers, commercially pure titanium, titanium alloys, CoCr alloys, nickel titanium (nitinol) alloys and implant grade stainless steels.

Referring to FIGS. 1 and 2, assembly of PDI system 100 may begin by loading prosthesis 200 into delivery needles 106 and 108. In particular, first end portion 202 may be inserted into first open channel 107. Likewise, second end portion 204 may be inserted into second open channel 109. Following this, impact members 130 and 132 may be inserted into open channels 107 and 109, respectively. At this point, PDI system 100, including delivering needles 106 and 108 as well as impact members 130 and 132 and prosthesis 200 may be inserted into delivery lumen 102. Generally, delivery needles 106 and 108 may be inserted through delivery lumen 102 until needle ends 120 and 122 are disposed just within distal end portion 152 of delivery lumen 102. As seen in FIG. 1, distal end portions 142 and 143 of impact members 130 and 132, respectively, preferably extend out of proximal end portion 150 of delivery lumen 102. It should be understood that the order of assembling the components of PDI system 100 is intended to be exemplary. In other embodiments, the order of assembly may vary. Additionally, it should be understood that PDI system 100 may be associated with a delivery cannula at various times. In some cases, PDI system 100 may be inserted into the delivery lumen of the delivery cannula prior to moving the delivery cannula into position near a tissue to be treated. In other case, PDI system 100 may be inserted into the delivery lumen after moving the delivery cannula into position near the tissue to be treated.

FIGS. 3-8 illustrate a method of implanting prosthesis 200 using PDI system 100 in order to reattach first tissue 300 to second tissue 302. The current embodiment is intended to be generic and could be applied to various different situations in which one tissue must be reattached to a second tissue. For example, in some cases, first tissue 300 may be a tendon and second tissue 302 may be a bone. In this case, second tissue 302 could be any bone in the body and first tissue 300 could be any associated tendon configured to attach to second tissue 302. In other cases, first tissue 300 and second tissue 302 could be similar types of tissue.

Generally, delivery cannula 101 may be inserted into an incision of a patient. Throughout the remainder of this detailed description it should be understood that this method for repairing tissue using PDI system 100 may include various additional steps often associated with arthroscopic surgery. In some embodiments, an arthroscope or similar device may be inserted into a second incision in the skin of the patient. With this arrangement, a surgeon may visualize the tissue requiring repair through video taken with the arthroscope.

Figure 3:
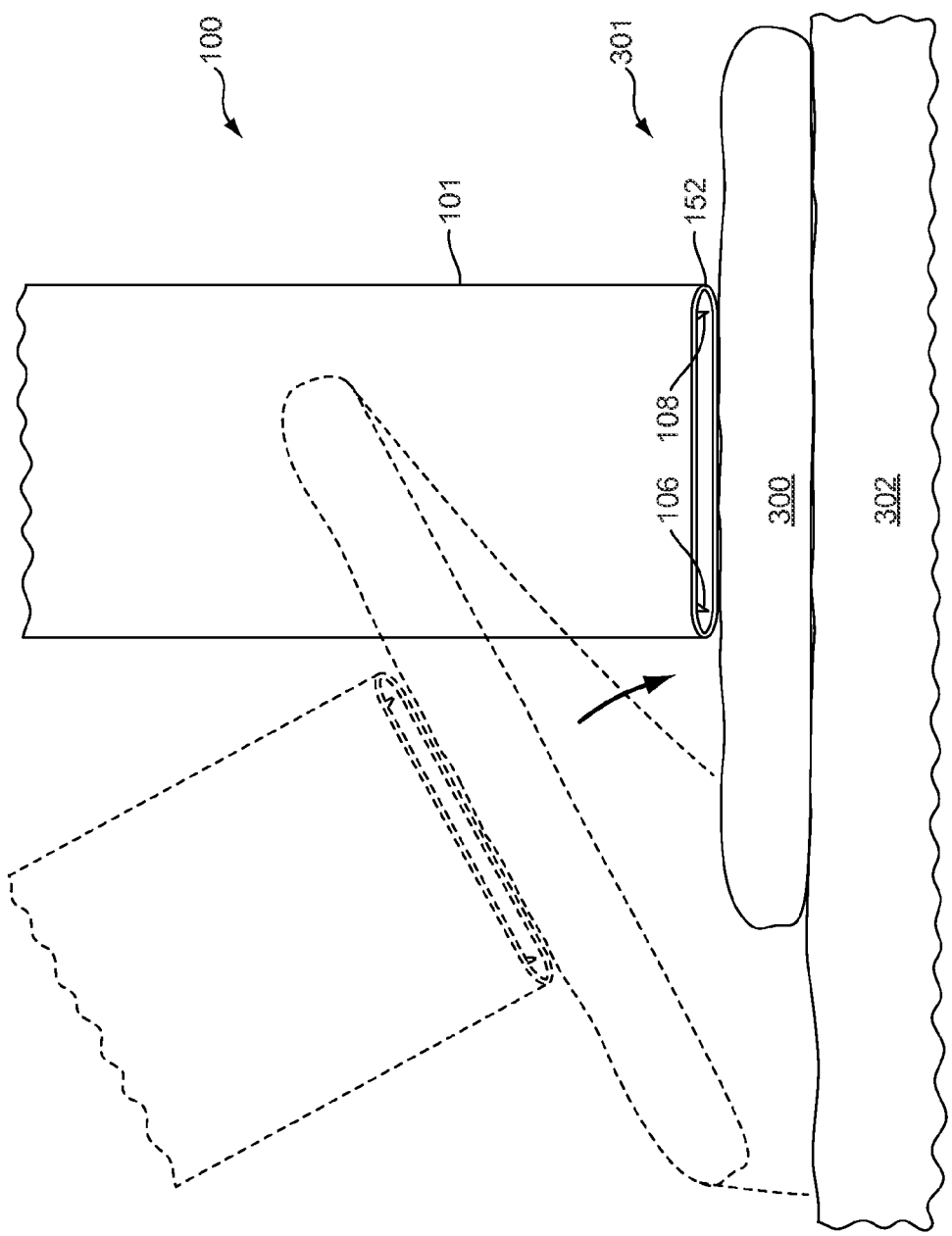
FIG. 3 is a schematic view of a preferred embodiment of a delivery cannula associating with a treatment area.

Referring to FIG. 3, delivery cannula 101 may initially be disposed in treated area 301. The term "treated area" as used through this detailed description and in the claims refers to the region of a tissue that may be repaired using PDI system 100. Using distal end portion 152 of delivery cannula 101, first tissue 300 may be pressed against second tissue 302 to set first tissue 300 in place prior to implantation. Preferably, at this point, delivery needles 106 and 108 are disposed just within distal end portion 152 so that delivery cannula 101 presents a generally blunt surface to first tissue 300. This may help prevent any tearing of first tissue 300 with PDI system 100.

Figure 4:
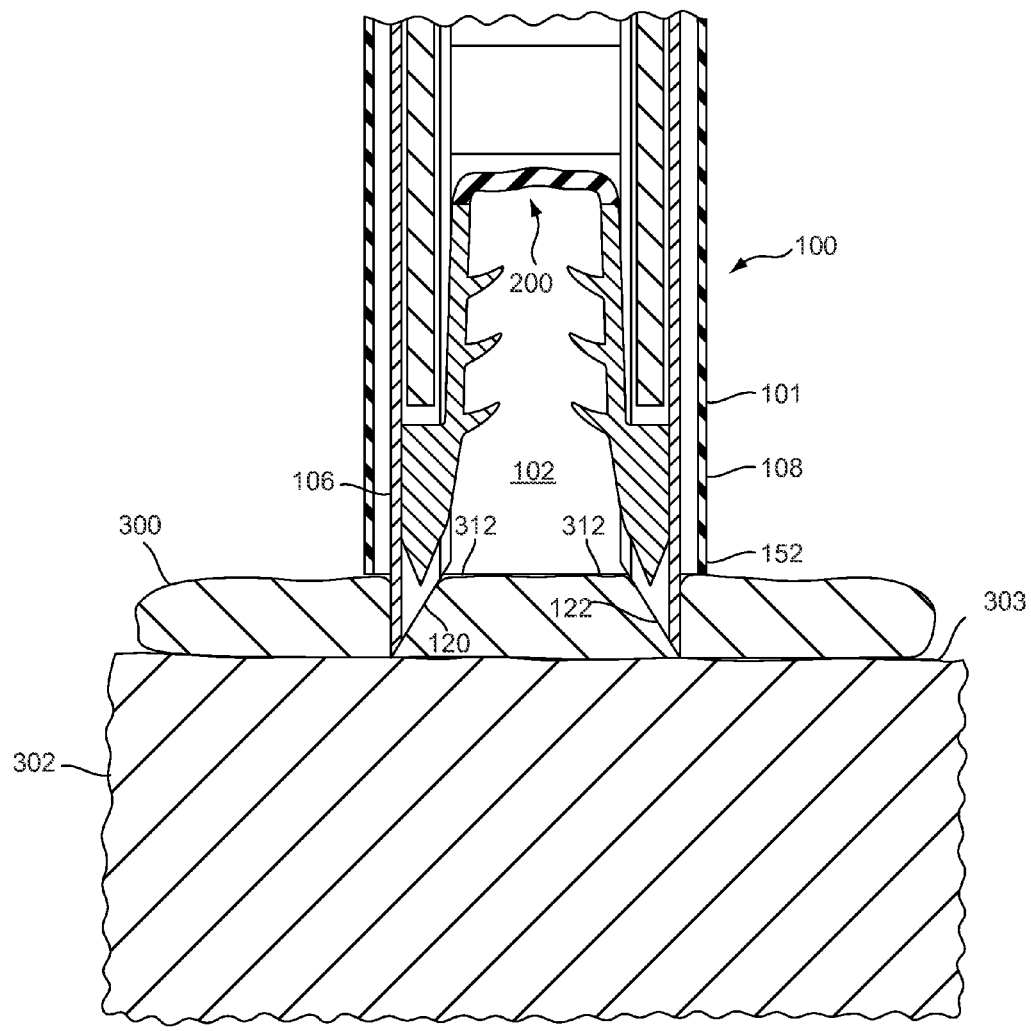
FIG. 4 is a cross sectional view of a preferred embodiment of a prosthesis delivery and implantation system associating with a first tissue and a second tissue.

Referring to FIG. 4, delivery needles 106 and 108 may be displaced from distal end portion 152 of delivery lumen 102. In some embodiments, needle ends 120 and 122 may be used to precisely locate PDI system 100 on second tissue 302. In some cases, needle ends 120 and 122 may provide points of contact between PDI system 100 and second tissue 302 to substantially reduce any movement of PDI system 100 with respect to second tissue 302. In this preferred embodiment, needle ends 120 and 122 do not substantially pierce second tissue 302 and only contact outer surface 303 of second tissue 302. However, needle ends 120 and 122 may pierce through first tissue 300 at first portion 310 and second portion 312.

Figure 8:
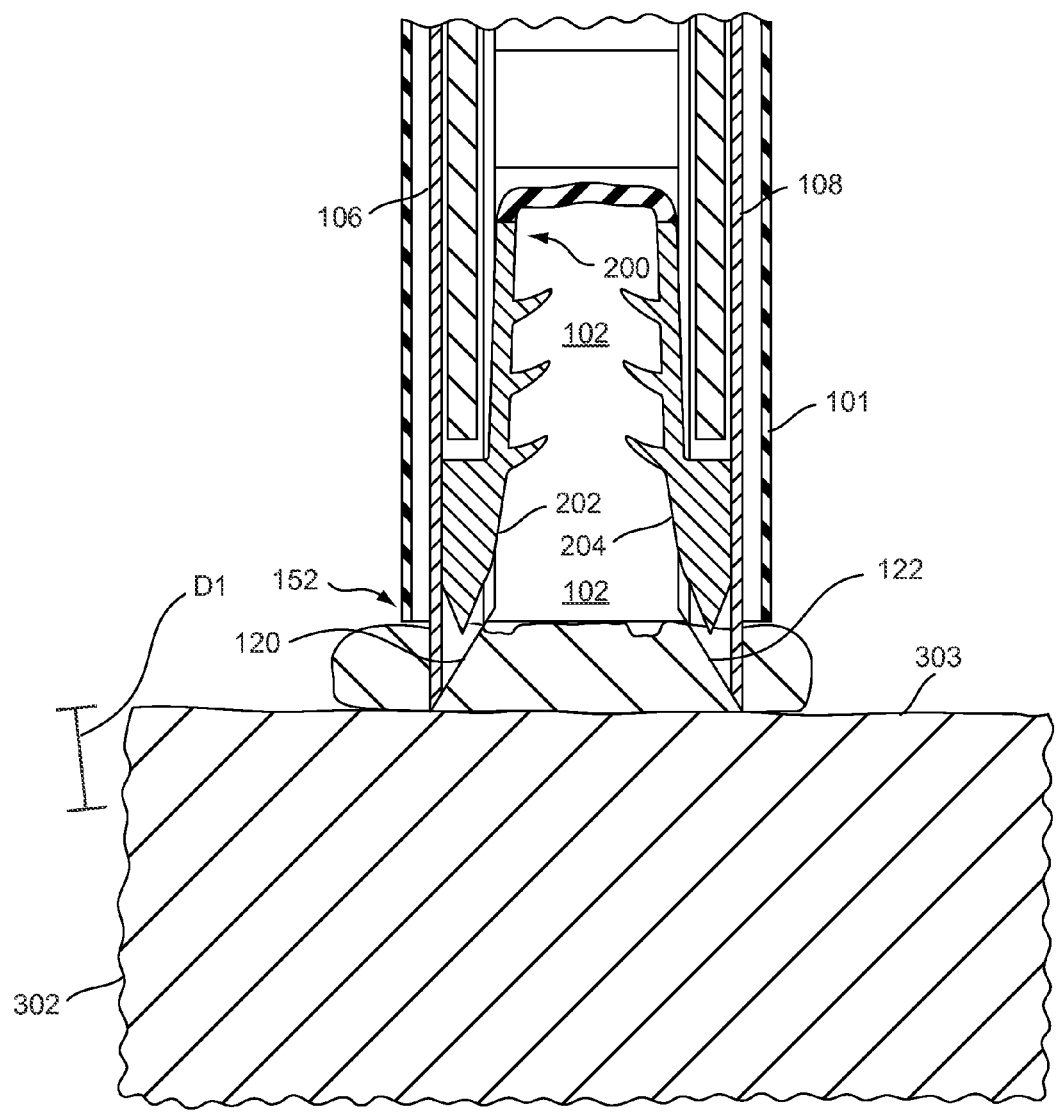
FIG. 8 is a cross sectional view of a preferred embodiment of a prosthesis delivery and implantation system with delivery needles penetrating through a first tissue and a second tissue.

In an alternative embodiment, seen in FIG. 8, needle ends 120 and 122 may penetrate into second tissue 302. Generally, needle ends 120 and 122 may penetrate by any desired amount. In some embodiments, needle ends 120 and 122 may penetrate into second tissue 302 a distance D1 below outer surface 303. In some cases, the value of distance D1 may vary in the range between 1 millimeter and 2 centimeters. In certain embodiments, the value of distance D1 is approximately 1 centimeter. With this arrangement, needle ends 120 and 122 may help facilitate the penetration of prosthesis 200 into second tissue 302 by creating holes in which end portions 202 and 204 or prosthesis 200 may be inserted.

Figure 5:
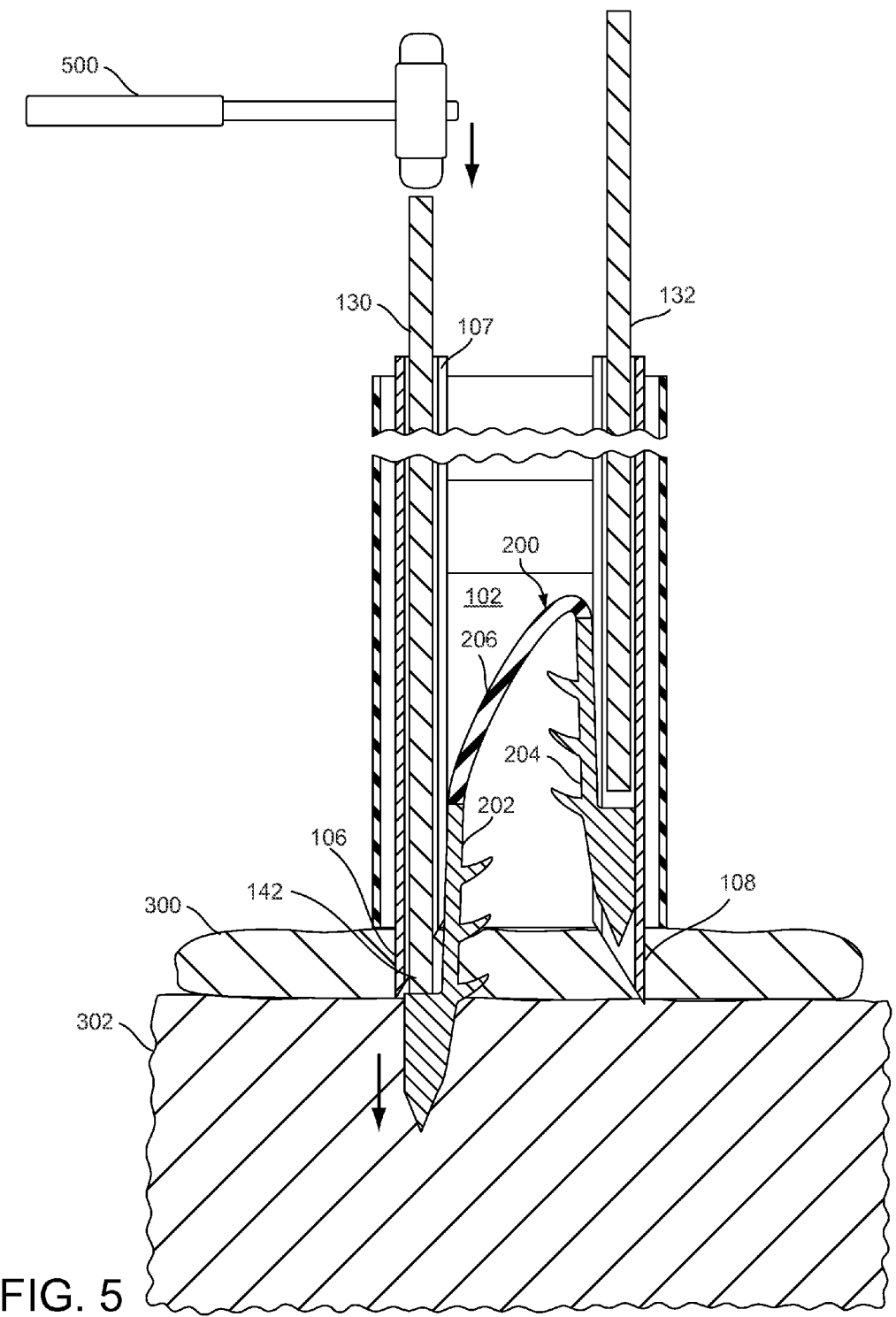
FIG. 5 is a cross sectional view of a preferred embodiment of a first impact member of a prosthesis delivery and implantation system delivering a first force to a first end portion of a prosthesis.
Figure 6:
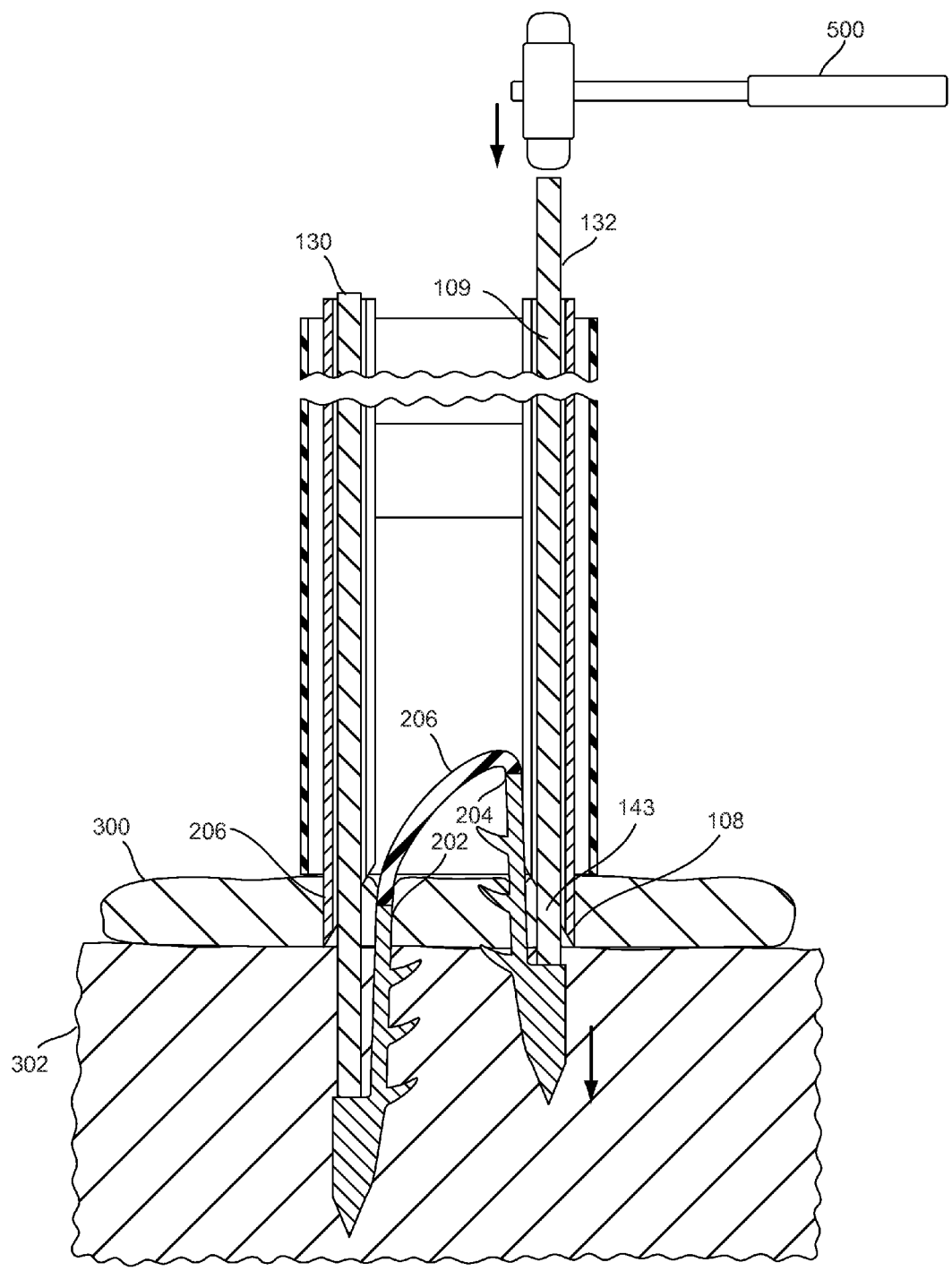
FIG. 6 is a cross sectional view of a preferred embodiment of a second impact member of a prosthesis delivery and implantation system delivering a second force to a second end portion of a prosthesis.

Referring to FIGS. 5 and 6, it may be preferable to drive end portions 202 and 204 into tissues 300 and 302 independently. In this case, tool 500 may be used to apply a first force to first impact member 130. As first impact member 130 is driven distally through first open channel 107, first distal end portion 142 of first impact member 130 may be configured to drive first end portion 202 through tissues 300 and 302. As seen in FIG. 5, second end portion 204 of prosthesis 200 remains in place since second impact member 132 does not move and central portion 206 deforms without transferring force to second end portion 204.

Referring now to FIG. 6, tool 500 may be used to apply a second force to second impact member 132. As second impact member 132 is driven distally through second open channel 109, second distal end portion 143 of second impact member 132 may be configured to drive second end portion 204 of prosthesis 200 through tissues 300 and 302. As seen in FIG. 6, first end portion 202 of prosthesis 200 remains in place since first impact member 132 does not move at this point and central portion 206 can deform without transferring force to first end portion 202. Preferably, the process illustrated in FIGS. 5 and 6 is repeated until both end portions 202 and 204 are fully implanted. With this arrangement, first end portion 202 may be implanted substantially prior to the implantation of second end portion 204 rather than simultaneously with second end portion 204.

By applying a first force to first impact member 130, the distal motion of first impact member 130 displaces first end portion 202 of prosthesis 200 distally and eventually displaces first end portion 202 from first delivery needle 106. At this point, first end portion 202 may be fully implanted into tissues 300 and 302. Also, by applying a second force to second impact member 130, the distal motion of second impact member 132 displaces second end portion 204 of prosthesis 200 and eventually displaces second end portion 204 form second delivery needle 108. At this point, second end portion 202 may be fully implanted into tissues 300 and 302. As previously discussed, projections 212 may facilitate anchoring end portions 202 and 204 as prosthesis 200 is implanted into second tissue 302.

Using this arrangement, first end portion 202 and second end portion 204 may be driven into tissues 300 and 302 independently, to provide for increased control over the implantation of prosthesis 200. This method may be advantageous over prior methods that require implantation of two ends of a prosthesis simultaneously. Additionally, because central portion 206 is partially deformable, end portions 202 and 204 could be driven to slightly different depths within second tissue 302 by applying different forces to first impact member 130 and second impact member 132.

Figure 9:
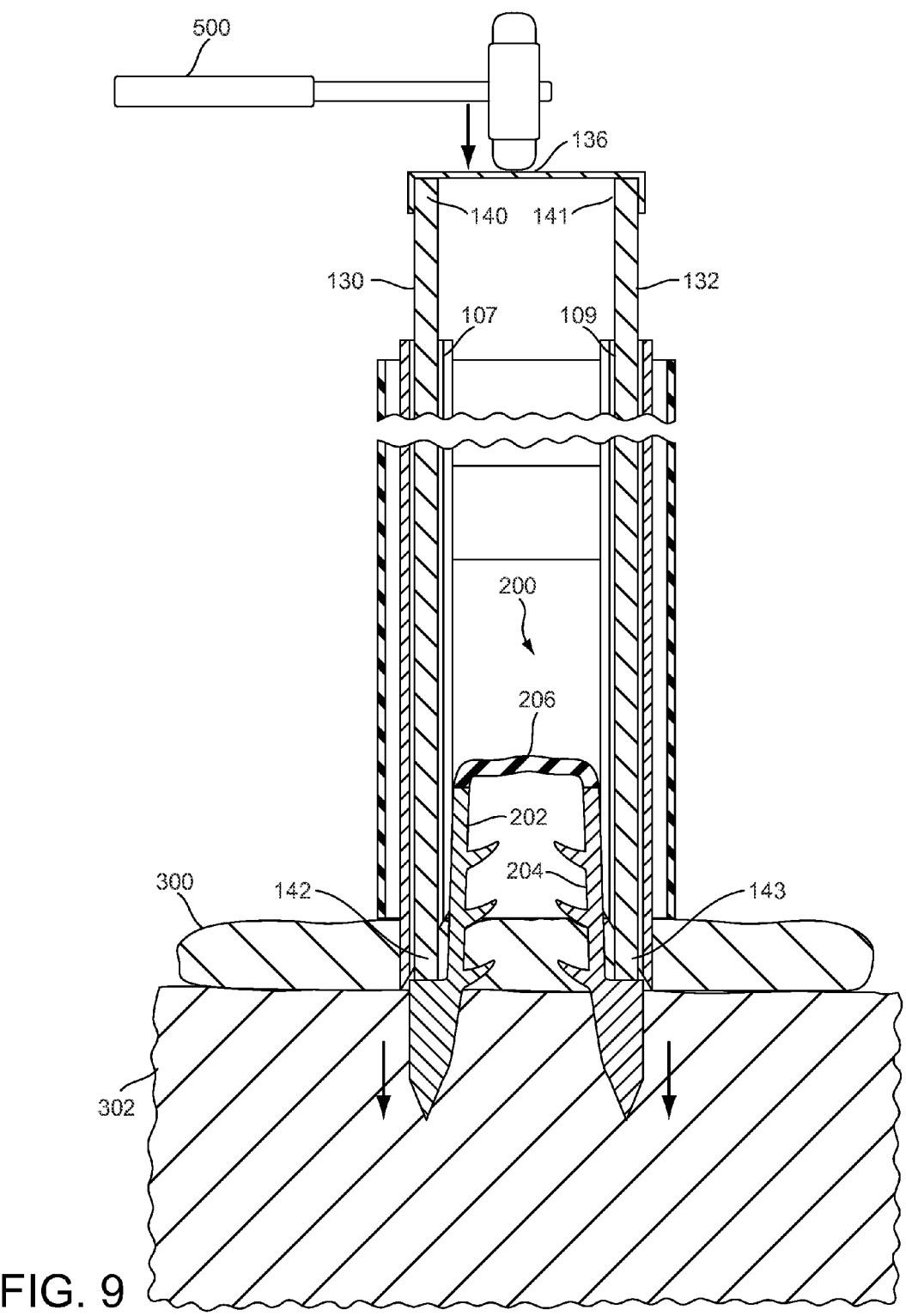
FIG. 9 is a cross sectional view of a preferred embodiment of two impact members of a prosthesis delivery and implantation system delivering forces to end portions of a prosthesis.

In an alternative embodiment, seen in FIG. 9, impact members 130 and 132 may be rigidly attached using connecting member 136. In this embodiment, connecting member 136 may be a cap that slides over impact members 130 and 132 at proximal end portions 140 and 141, respectively. In other embodiments, a connecting member could include a fastener that can be disconnected to allow impact members 130 and 132 to move independently of one another. For example, in other embodiments, the connecting member could include a hinge. In still other embodiments, other mechanisms for attaching and detaching impact members 130 and 132 could also be used.

Using connecting member 136, a driving force may be applied to impact members 130 and 132 simultaneously. In this alternative embodiment, impact members 130 and 132 are rigidly attached via connecting member 136. As a driving force is applied to connecting member 136 and impact members 130 and 132 using tool 500, impact members 130 and 132 are configured to move in a distal direction through open channels 107 and 109. In particular, distal end portions 142 and 143 are configured to impact first end portion 202 and second end portion 204 of prosthesis 200. This impact helps to drive end portions 202 and 204 of prosthesis 200 distally through first tissue 300 and into second tissue 302. Preferably, the driving force provided by tool 500 may be reapplied many times until first end portion 202 and second end portion 204 are fully driven into second tissue 302. As previously discussed, projections 212 may facilitate anchoring end portions 202 and 204 as prosthesis 200 is implanted into second tissue 302.

Figure 7:
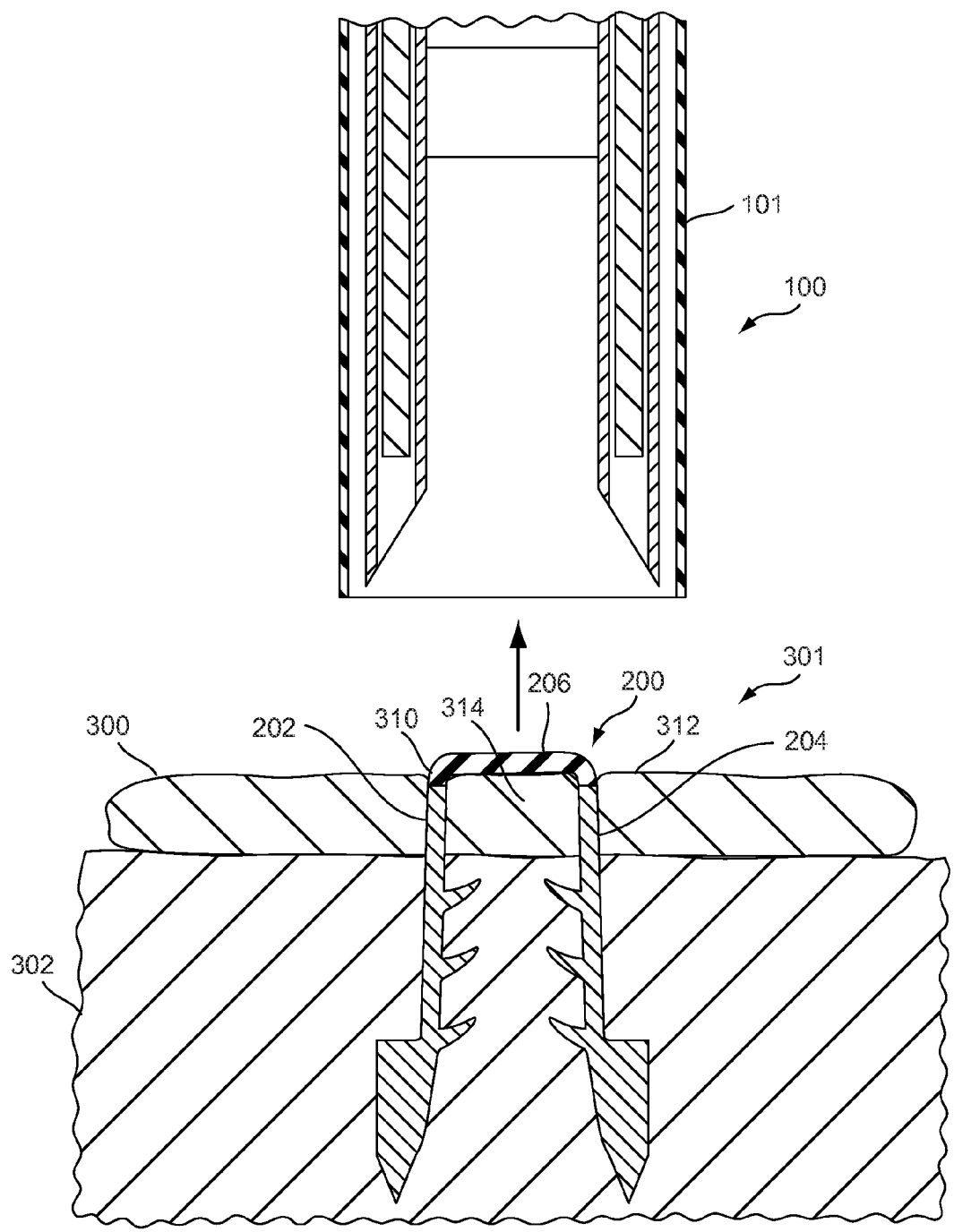
FIG. 7 is a cross sectional view of a preferred embodiment of a prosthesis fully implanted into a first tissue and a second tissue.

Referring to FIG. 7, following the implantation of prosthesis 200, PDI system 100 may be removed from treatment area 301. As seen in this Figure, first portion 310 of first tissue 300 has been attached to second tissue 302 by first end portion 202 of prosthesis 200. Likewise, second portion 312 of first tissue 300 has been attached to second tissue 302 by second end portion 204 of prosthesis 200. With this arrangement, first tissue 300 may be fixedly attached to second tissue 302 to help facilitate healing of treatment area 301.

Preferably, prosthesis 200 is also configured to hold additional portions of tissue 300 in place with respect to second tissue 302. In this embodiment, first tissue 300 further includes intermediate portion 314 that is disposed between first portion 310 and second portion 312. As end portions 202 and 204 are implanted into second tissue 302, central portion 206 may be configured to wrap around a portion of intermediate portion 314. As previously discussed, central portion 206 is configured to be flexible and preferably generally conforms to the shape of intermediate portion 314. Furthermore, end portions 202 and 204 may apply tension to central portion 206 that may be used to tightly fasten intermediate portion 314 in place. With this arrangement, multiple portions of first tissue 300 may be fixed in place with respect to second tissue 302 without the use of additional end portions for implantation through tissues 300 and 302. In some cases, this arrangement may help maintain a strong connection between tissues 300 and 302.

In some embodiments, a PDI system may be operated without the use of a cannula. For example, in some cases a surgeon may repair a portion of tissue that is disposed close to the surface of the skin, such as a bone or tendon in a foot or a hand. In this case, the PDI system, including first and second driving needles, first and second impact members and a prosthesis, may be directly associated with the tissue without the use of a cannula. In particular, the driving needles may be located at the treatment area and the impact members may be used to drive the prosthesis into the tissue.

In another embodiment, a prosthesis may be implanted without the use of a set of delivery needles. Instead, a set of impact members may be configured to align with portions of the first end portion and the second end portion of the prosthesis using other provisions. In some cases, for example, a distal portion of an impact member could associate with an end portion of a prosthesis using a magnetic coupling. In other cases, the impact member could be associated with the end portion using a light adhesive. In still other cases, other types of provisions could be used to associate and align an impact member with an end portion of a prosthesis. Using this arrangement, a first impact member may include a first distal portion that may be configured to align and associate with a first end portion of a prosthesis. Likewise, a second impact member may include a second distal portion that may be configured to align and associate with a second end portion of the prosthesis. With this arrangement, the first and second impact members may be used to drive the first and second end portions of the prosthesis directly into one or more tissues without the use of delivery needles.

FIGS. 10-18 are intended to illustrate specific examples of tissue systems that may be repaired using PDI system 100. It should be understood that the following embodiments are not intended to be limiting and other uses for PDI system 100 would be apparent to anyone skilled in the art. As previously discussed, PDI system 100 may be used with any type of tissue that requires repair and that is configured to receive prosthesis 200. Furthermore, the following embodiments illustrate various applications of prosthesis 200 to tissue systems and do not include steps for implanting prosthesis 200 which have already been discussed in the previous embodiments. It should be understood that in each of the following examples, prosthesis 200 can be implanted into one or more tissues using PDI system 100 by following steps substantially similar to those previously discussed.

In some embodiments, PDI system 100 may be used for attaching a portion of bone that has broken away from a bone structure. In some cases, PDI system 100 may be used to implant end portions 202 and 204 of prosthesis 200 through the portion of bone and into the bone structure. In other cases, PDI system 100 could be used to implant end portions 202 and 204 of prosthesis only into the bone structure in a manner that holds the portion of bone in place with respect to the bone structure using central portion 206 of prosthesis 200. In a preferred embodiment, PDI system 100 may be used to deliver and implant end portions 202 and 204 of prosthesis 200 into the portion of bone and the bone structure and also may apply tension to the substantial entirety of the portion of bone with central portion 206.

Figure 10:
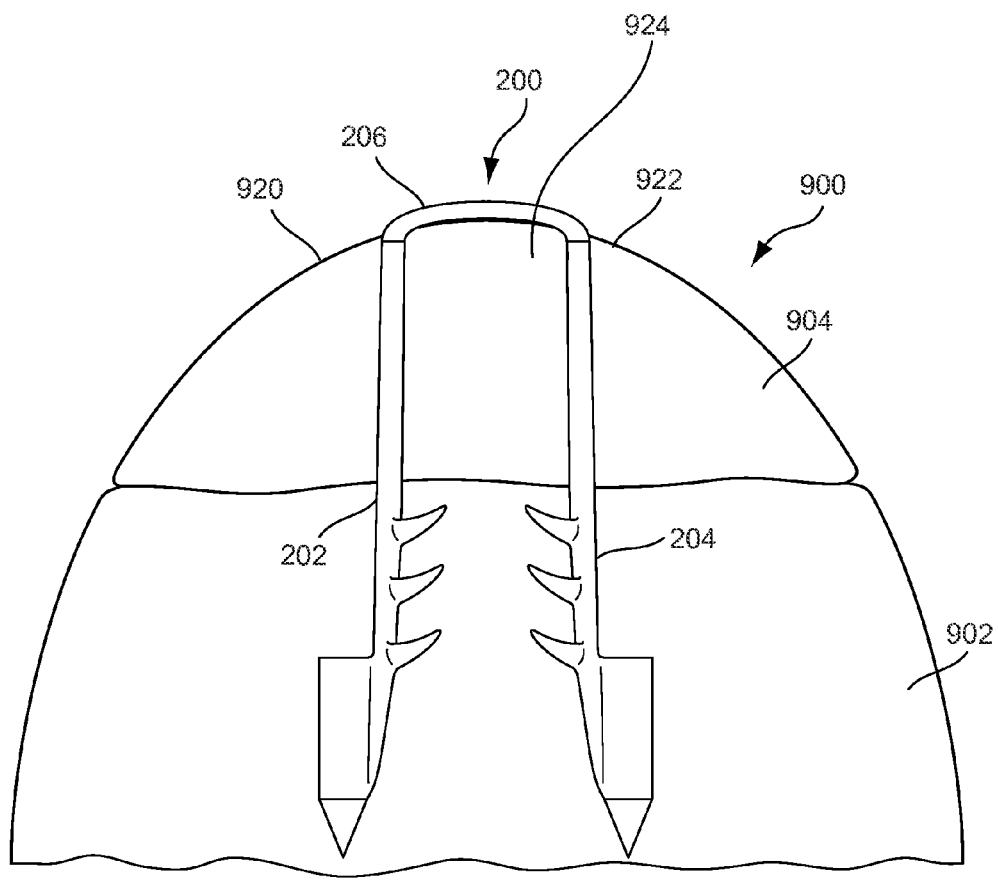
FIG. 10 is a schematic view of a preferred embodiment of a prosthesis configured to attach a first portion of a bone to a bone structure.

Referring to FIG. 10, prosthesis 200 may be used to repair tissue system 900 that comprises bone 902 and portion of bone 904. In this case, portion of bone 904 has fractured off of bone 902 and requires reattachment. In this embodiment, first end portion 202 and second end portion 204 have been implanted through portion of bone 904 and bone 902 using PDI system 100 in order to facilitate healing. In particular, first end portion 202 has been inserted through first portion 920 of portion of bone 904 and second end portion 202 has been inserted through second portion 922 of portion of bone 904. Additionally, central portion 206 has conformed to, and applied tension across, intermediate portion 924 of portion of bone 904. With this arrangement, prosthesis 200 is configured to facilitate the reattachment of portion of bone 904 to bone 902 to repair tissue system 900.

Figure 11:
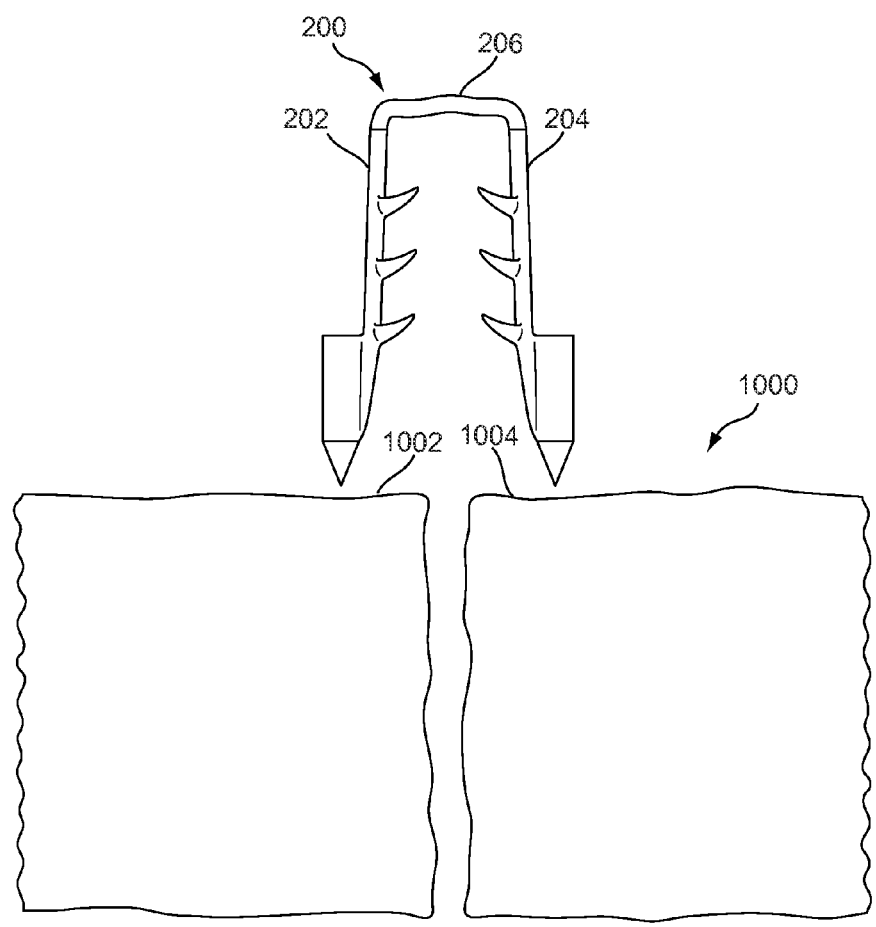
FIG. 11 is a schematic view of a preferred embodiment of a prosthesis configured to attach to a first fractured portion of a bone and a second fractured portion of a bone prior to implantation.
Figure 12:
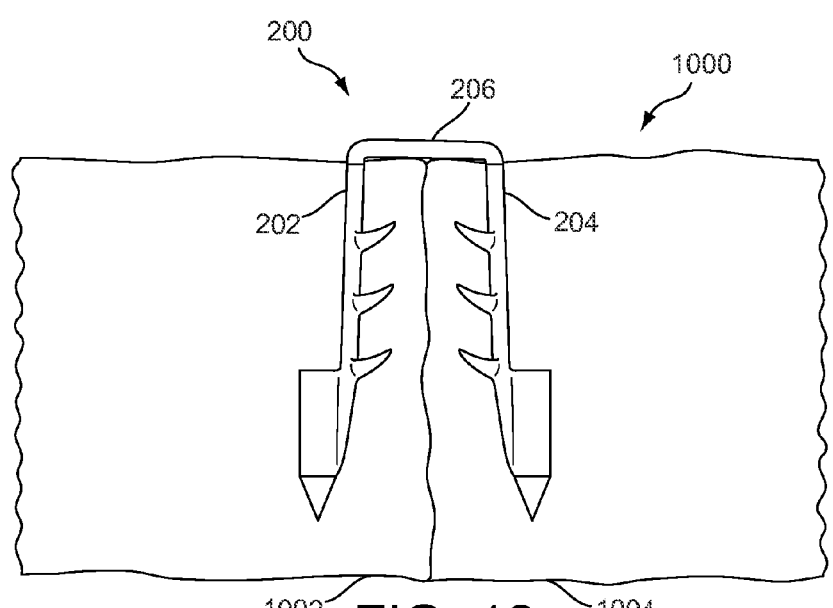
FIG. 12 is a schematic view of a preferred embodiment of a prosthesis configured to attach to a first fractured portion of a bone and a second fractured portion of a bone post implantation.

Referring to FIGS. 11-12, prosthesis 200 may also be used to help repair first fractured end 1002 and second fractured end 1004 of bone 1000 that have separated, or to fuse two adjacent bones 1002 and 1004. As indicated schematically, prosthesis 200 may be applied to first fractured end 1002 and second fractured end 1004 using PDI system 100. In this case, first end portion 202 may be configured to implant into first fractured end 1002. Likewise, second end portion 204 may be configured to implant into second fractured end 1004. With this arrangement, first fractured end 1002 and second fractured end 1004 may be secured against one another under the tension of central portion 206. As fractured ends 1002 and 1004 are fixed in place using prosthesis 200, new bone growth between ends 1002 and 1004 may help permanently repair bone 1000.

Figure 13:
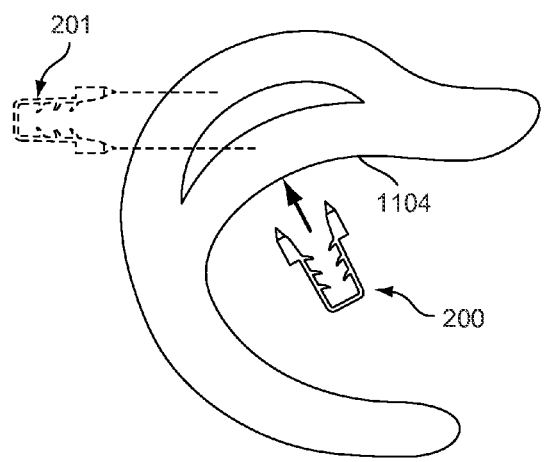
FIG. 13 is top down isometric view of a preferred embodiment of a prosthesis configured to repair a circumferential tear in a medial meniscus in a pre-operating condition.
Figure 14:
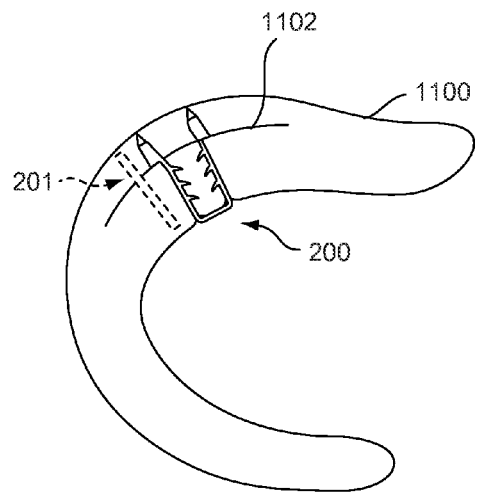
FIG. 14 is a top down view of a preferred embodiment of a prosthesis configured to repair a circumferential tear in a medial meniscus is a post-operating condition.

Referring to FIGS. 13-16, prosthesis 200 may be used to repair one or more portions of meniscus 1100. FIG. 13 illustrates a preferred embodiment of a meniscus 1100 with circumferential tear 1102 in a pre-operative state. In some cases, prosthesis 201 may be applied in an axial or vertical direction to circumferential tear 1102. In a preferred embodiment, prosthesis 200 may be applied along interior portion 1104 of meniscus 1100 in order to facilitate the repair of circumferential tear 1102. FIG. 14 illustrates meniscus 1100 in a post-operative state. In this case, prosthesis 200 has been applied radially across circumferential tear 1102 and meniscus 1100 may be allowed to heal. Additionally, in this embodiment, prosthesis 201 has been applied over circumferential tear 1102 in an axial direction.

Figure 15:
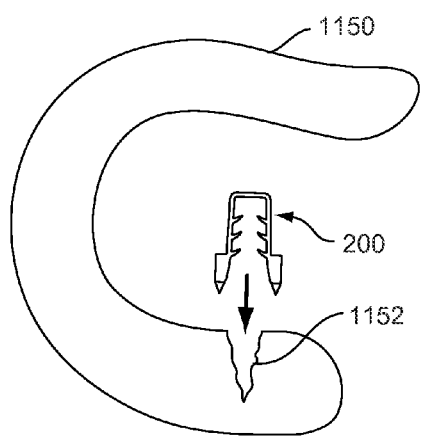
FIG. 15 is top down isometric view of a preferred embodiment of a prosthesis configured to repair a radial tear in a medial meniscus in a pre-operating condition.
Figure 16:
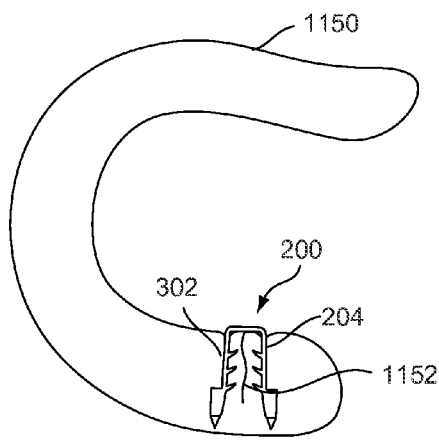
FIG. 16 is a top down view of a preferred embodiment of a prosthesis configured to repair a radial tear in a medial meniscus is a post-operating condition.

Referring to FIGS. 15-16, prosthesis could also be applied to meniscus 1150 that requires repair for radial tear 1152. FIG. 15 shows meniscus 1150 with radial tear 1152 in a pre-operative state, before prosthesis 200 has been applied using PDI system 100. In FIG. 16, prosthesis 200 has been applied to repair radial tear 1152. In particular, first end portion 202 and second end portion 204 are disposed on opposing sides of radial tear 1152. With this arrangement, radial tear 1152 may be pinched together and allowed to heal.

Figure 17:
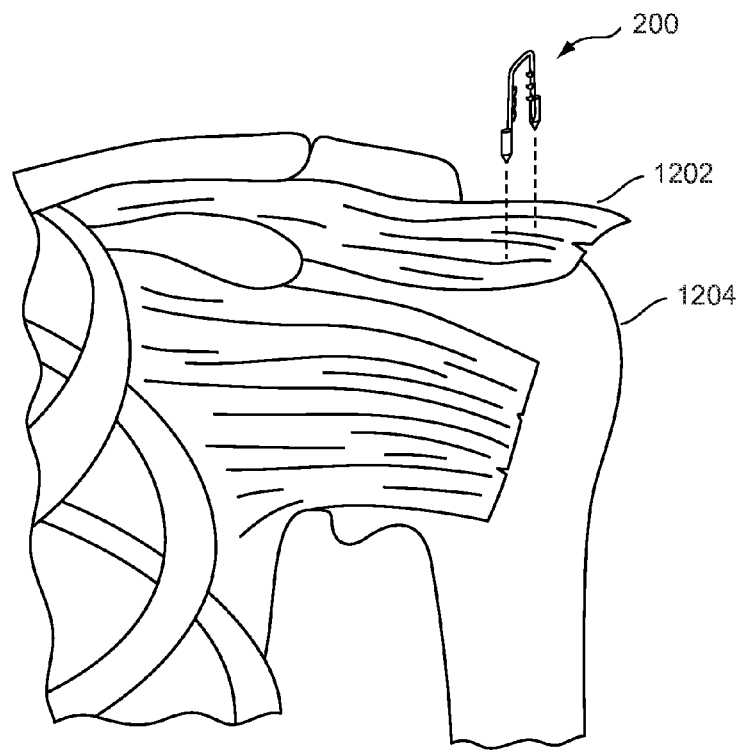
FIG. 17 is a plan view of a preferred embodiment of a prosthesis configured to attach a tendon to a humerus bone in a pre-operating condition.
Figure 18:
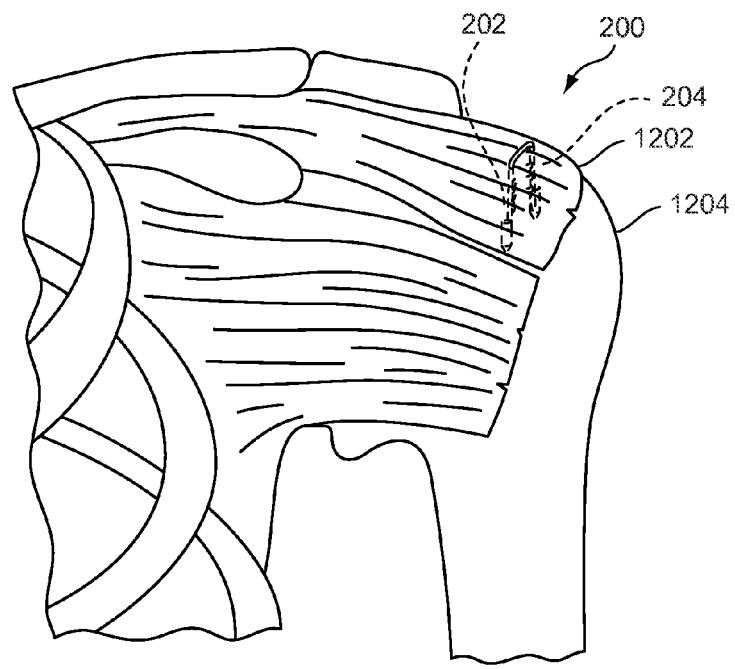
FIG. 18 is a plan view of a preferred embodiment of a prosthesis configured to attach a tendon to a humerus bone in a post-operating condition.

Referring to FIGS. 17 and 18, prosthesis 200 may be applied to tendon 1202 that has detached from humerus 1204. This situation is common in rotator cuff injuries. FIG. 17 illustrates detached tendon 1202 in a pre-operative state. FIG. 18 illustrates tendon 1202 attached to humerus 1204 in a post-operative state using prosthesis 200. In particular, first end portion 202 and second end portion 204 of prosthesis 200 have preferably inserted through tendon 1202 and been implanted into humerus 1204.

For clarity, the previous embodiments illustrated in FIGS. 11-18 only show the use of a single prosthesis to repair different types of tissue. It should be understood that in other embodiments, any number of prosthesis could be applied simultaneously to repair one or more tissues. For example, in some cases, two prostheses could be used to repair a tissue. In other cases, more than two prostheses could be used to repair a tissue. Additionally, any shapes and/or orientations of one or more prostheses may be used in other embodiments. For example, in some cases an X-shaped configured of two prostheses could be used. In other embodiments, various other types of geometric shapes or patterns may be formed using multiple prostheses. Using multiple prostheses in various shapes and patterns may allow a surgeon to obtain the desired tension and attachment configuration for the prostheses to promote healing of the damaged tissue.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A prosthesis delivery and implantation system comprising:
   a delivery cannula having a distal end portion, the distal end portion of the delivery cannula configured for placement near a treated area;
   the delivery cannula having a delivery lumen;
   a prosthesis delivery system disposed in the delivery cannula;
   the prosthesis delivery system including a first delivery needle, a second delivery needle, and a spacing web connecting the first delivery needle to the second delivery needle;
   a prosthesis having a first end portion, a central portion, and a second end portion;
   wherein the prosthesis delivery system is configured to retain and deliver the prosthesis;
   the first delivery needle being generally hollow and having a first open channel in which the first end portion of the prosthesis is disposed;
   the second delivery needle being generally hollow and having a second open channel in which the second end portion of the prosthesis is disposed;
   a first impact member disposed within the first open channel of the first delivery needle;
   wherein the first impact member transfers a first force to the first end portion of the prosthesis;
   a second impact member disposed within the second open portion of the second delivery needle;
   wherein the second impact member transfers a second force to the second end portion of the prosthesis;
   wherein the first open channel of the first delivery needle defines a first longitudinal axis;
   wherein the second open channel of the second delivery needle defines a second longitudinal axis;
   wherein the first end portion of the prosthesis has a first distal anchor portion that projects from a remainder of the first end portion in a direction lateral to the first longitudinal axis so as to define a first impact surface;

wherein the second end portion of the prosthesis has a second distal anchor portion that projects from a remainder of the second end portion in a direction lateral to the second longitudinal axis so as to define a second impact surface;

wherein the first impact member transfers the first force to the first end portion of the prosthesis by pushing against the first impact surface; and wherein the second impact member transfers the second force to the second end portion of the prosthesis by pushing against the second impact surface.

2. The system according to claim 1, wherein the first impact member and the second impact member are rigidly associated such that the first impact member and the second impact member are capable of being driven generally simultaneously.

3. The system according to claim 1, wherein the first impact member and the second impact member are capable of relative motion with respect to one another and wherein the first impact member may be moved independently of the second impact member.

4. The system according to claim 1, wherein distal motion of the first impact member displaces the first end portion of the prosthesis distally and eventually displaces the first end portion of the prosthesis out of the first delivery needle and implants the first end portion of the prosthesis into a tissue.

5. The system according to claim 4, wherein the central portion of the prosthesis is flexible to accommodate relative motion between the first end portion of the prosthesis and the second end portion of the prosthesis.

6. The system according to claim 5, wherein the second end portion of the prosthesis is displaced distally away from the second delivery needle by the second impact member after the first end portion of the prosthesis is implanted.

7. The system according to claim 1, wherein the first impact member includes a distal end portion and a proximal end portion opposite to the distal end portion, wherein the distal end portion contacts the first end portion of the prosthesis, and wherein the proximal end portion receives the first force.

8. The system according to claim 1, wherein the central portion of the prosthesis is deformable such that the central portion deforms a first time while implanting the first end portion independently of the second end portion and a second time while implanting the second end portion independently of the first end portion.

9. The system according to claim 1, further comprising a disconnectable connecting member that rigidly connects the first impact member to the second impact member.

10. The system according to claim 9, wherein the disconnectable connecting member comprises a cap disposed over a proximal end of the first impact member and a proximal end of the second impact member.

11. The system according to claim 9, wherein the disconnectable connecting member comprises a hinged disconnectable connecting member.

12. The system according to claim 1, wherein the first and second delivery needles hold the respective first and second impact members apart from each other at a fixed distance lateral to an implantation direction.

13. The system according to claim 1, wherein the prosthesis delivery system holds the prosthesis such that the first end portion, the central portion, and the second end portion are substantially coplanar.

14. The system according to claim 1, wherein each of the first and second distal anchor portions is cylindrical and each of the first and second impact surfaces is circular.

15. The system according to claim 14, wherein an end of the first distal anchor portion opposite to the first impact surface is pointed, and wherein an end of the second distal anchor portion opposite to the second impact surface is pointed.

16. The system according to claim 15, wherein the remainder of the first end portion has at least one first projection;

wherein the remainder of the second end portion has at least one second projection;

wherein when the prosthesis is disposed in the first and second delivery needles:
the first end portion of the prosthesis is generally parallel to the second end portion of the prosthesis;
the central portion of the prosthesis is generally transverse to the first end portion and the second end portion; and
the at least one first projection and the at least one second projection extend toward each other and distally toward the central portion of the prosthesis.

17. A prosthesis delivery and implantation system comprising:

a delivery cannula having a distal end portion, the distal end portion of the delivery cannula configured for placement near a treated area;

the delivery cannula having a delivery lumen;

a prosthesis delivery system disposed in the delivery cannula;

the prosthesis delivery system including a first delivery needle, a second delivery needle, and a spacing web disposed between the first delivery needle and the second delivery needle;

a prosthesis having a first end portion, a central portion, and a second end portion;

wherein the prosthesis delivery system is configured to retain and deliver the prosthesis;

the first delivery needle being generally hollow and having a first open channel configured to accommodate the first end portion of the prosthesis;

the second delivery needle being generally hollow and having a second open channel configured to accommodate the second end portion of the prosthesis;

wherein the prosthesis delivery system allows the first end portion to be implanted substantially prior to the implantation of the second end portion;

wherein the first open channel of the first delivery needle defines a first longitudinal axis;

wherein the second open channel of the second delivery needle defines a second longitudinal axis;

wherein the first end portion of the prosthesis has a first distal anchor portion that projects from a remainder of the first end portion in a direction lateral to the first longitudinal axis so as to define a first impact surface;

wherein the second end portion of the prosthesis has a second distal anchor portion that projects from a remainder of the second end portion in a direction lateral to the second longitudinal axis so as to define a second impact surface;

wherein a first impact member disposed within the first open channel of the first delivery needle pushes against the first impact surface of the first end portion of the prosthesis; and wherein a second impact member disposed within the second open channel of the second delivery needle pushes against the second impact surface of the second end portion of the prosthesis.

18. The system according to claim 17, wherein the prosthesis is moved distally by moving the first impact member disposed within the first open channel of the first delivery needle and by moving the second impact member disposed within the second open channel of the second delivery needle.

19. The system according to claim 18, wherein the first impact member and the second impact member move independently of each other, such that the first impact member moves in response to a first force applied to the first impact member, and the second impact member subsequently moves in response to a second force applied to the second impact member after the first force has been applied to the first impact member.

20. The system according to claim 17, wherein the central portion of the prosthesis is deformable such that the central portion deforms a first time while implanting the first end portion independently of the second end portion and a second time while implanting the second end portion independently of the first end portion.

21. The system according to claim 17, wherein the first delivery needle and the second delivery needle are generally linear and are positioned generally parallel to each other;
   wherein the first open channel of the first delivery needle comprises a C-shaped channel having a first opening facing the second delivery needle;
   wherein the second open channel of the second delivery needle comprises a C-shaped channel having a second opening facing the first delivery needle; and
   wherein the first opening and the second opening face each other.

22. The system according to claim 21, wherein the spacing web is attached to outer surfaces of the first and second delivery needles clear of the first and second openings and the prosthesis.

23. The system according to claim 17, wherein the prosthesis is configured to at least one of: attach a tendon to an associated bone, attach a first portion of bone to a second portion of bone, repair a meniscus, and repair a torn rotator cuff.

24. A prosthesis delivery and implantation system comprising:
   a prosthesis having a first end portion, a central portion, and a second end portion;
   wherein the central portion is deformable and wherein the first and second end portions are more rigid than the central portion;
   a prosthesis delivery system including a first delivery needle and a second delivery needle;
   the first delivery needle being generally hollow and having a first open channel in which the first end portion of the prosthesis is disposed;
   the second delivery needle being generally hollow and having a second open channel in which the second end portion of the prosthesis is disposed;
   a first impact member disposed within the first open channel of the first delivery needle and having a first distal end configured to associate and align with the first end portion;
   a second impact member disposed within the second open channel of the second delivery needle and having a second distal end configured to associate and align with the second end portion;
   wherein, at a first time, the first impact member moves in an implantation direction and applies a first force to the first end portion of the prosthesis, while the second impact member remains substantially stationary;
   wherein, at a second time subsequent to the first time, the second impact member moves in the implantation direction and applies a second force to the second end portion of the prosthesis, while the first impact member remains substantially stationary;
   wherein the central portion of the prosthesis deforms during a period between the first time and the second time;
   wherein the first open channel of the first delivery needle defines a first longitudinal axis;
   wherein the second open channel of the second delivery needle defines a second longitudinal axis;
   wherein the first end portion of the prosthesis has a first distal anchor portion that projects from a remainder of the first end portion in a direction lateral to the first longitudinal axis so as to define a first impact surface;
   wherein the second end portion of the prosthesis has a second distal anchor portion that projects from a remainder of the second end portion in a direction lateral to the second longitudinal axis so as to define a second impact surface;
   wherein the first impact member transfers the first force to the first end portion of the prosthesis by pushing against the first impact surface; and
   wherein the second impact member transfers the second force to the second end portion of the prosthesis by pushing against the second impact surface.

* * * * *